(12) United States Patent
Baumann et al.

(10) Patent No.: US 11,096,615 B2
(45) Date of Patent: Aug. 24, 2021

(54) ELECTRICAL PATCH FOR PHYSIOLOGICAL MEASUREMENTS

(71) Applicants: Eric Baumann, San Diego, CA (US); Habib Homayoun, Beaverton, OR (US); Lev Korzinov, San Diego, CA (US); David Churchville, San Diego, CA (US)

(72) Inventors: Eric Baumann, San Diego, CA (US); Habib Homayoun, Beaverton, OR (US); Lev Korzinov, San Diego, CA (US); David Churchville, San Diego, CA (US)

(*) Notice: Subject to any disclaimer, the term of this patent is extended or adjusted under 35 U.S.C. 154(b) by 698 days.

(21) Appl. No.: 15/155,073

(22) Filed: May 15, 2016

(65) Prior Publication Data

US 2016/0331257 A1 Nov. 17, 2016

Related U.S. Application Data

(60) Provisional application No. 62/161,884, filed on May 15, 2015, provisional application No. 62/309,230, (Continued)

(51) Int. Cl.
*A61B 5/25* (2021.01)
*G01S 19/13* (2010.01)
(Continued)

(52) U.S. Cl.
CPC .............. *A61B 5/25* (2021.01); *A61B 5/0022* (2013.01); *A61B 5/316* (2021.01); *A61B 5/6833* (2013.01); *G01R 31/382* (2019.01); *G01S 19/13* (2013.01); *G16H 40/67* (2018.01); *A61B 2560/0209* (2013.01); *A61B 2562/0219* (2013.01)

(58) Field of Classification Search
CPC ... A61B 5/0002; A61B 5/6833; A61B 5/0408; A61B 5/0022; A61B 5/04012; A61B 2560/0209; A61B 2562/0219; G16H 40/67; G01R 31/382; G01S 19/13
See application file for complete search history.

(56) References Cited

U.S. PATENT DOCUMENTS

2005/0227398 A1* 10/2005 Anderson ................ A61N 1/05
 438/36
2005/0228299 A1* 10/2005 Banet .................... A61B 5/1455
 600/485
(Continued)

*Primary Examiner* — Eun Hwa Kim
*Assistant Examiner* — Adam Z Minchella
(74) *Attorney, Agent, or Firm* — Mark Wisnosky

(57) ABSTRACT

An electrical patch and associated system for acquisition of physiological data is described. The patch has a design that enables a variety of configurations depending upon the requirements physiological measurements to be made. Patches with single input channels to patches with multiple input channels, processing capabilities and radio communication can all use the same physical configuration. The design includes a battery management system to enable long term data acquisition and an optimization process that includes mirroring of algorithms on the patch and devices local to the user with algorithms running on a centrally located server. The server can then optimize data acquisition and analysis algorithms. The components of the system and methods of use are included.

14 Claims, 18 Drawing Sheets

Related U.S. Application Data filed on Mar. 16, 2016, provisional application No. 62/309,300, filed on Mar. 16, 2016, provisional application No. 62/311,300, filed on Mar. 21, 2016.

(51) Int. Cl.
*A61B 5/00* (2006.01)
*G01R 31/382* (2019.01)
*G16H 40/67* (2018.01)
*A61B 5/316* (2021.01)

(56) References Cited

U.S. PATENT DOCUMENTS

| | | | |
|---|---|---|---|
| 2008/0091090 A1* | 4/2008 | Guillory | A61B 5/6814 600/301 |
| 2010/0234697 A1* | 9/2010 | Walter | A61B 5/291 600/301 |
| 2011/0066009 A1* | 3/2011 | Moon | A61B 5/0205 600/301 |
| 2011/0237924 A1* | 9/2011 | McGusty | A61B 5/6833 600/391 |
| 2011/0270049 A1* | 11/2011 | Katra | A61B 5/7246 600/301 |
| 2012/0101396 A1* | 4/2012 | Solosko | A61B 5/0006 600/509 |
| 2014/0303471 A1* | 10/2014 | Rajaraman | A61B 5/6833 600/393 |

\* cited by examiner

ELECTRICAL PATCH FOR PHYSIOLOGICAL MEASUREMENTS

CROSS-REFERENCE TO RELATED APPLICATIONS

This application claims priority to U.S. Provisional application 62/161,884, filed on 15 May 2015, titled "Electrical Patch for Biological Measurements", and, U.S. Provisional Application 62/309,230, filed on 16 Mar. 2016, titled "Electrical Patch for Biological Measurements", and, U.S. Provisional Application 62/309,300, filed 16 Mar. 2016 titled "Health Care Device with Battery Management System", and, U.S. Provisional Application 62/311,300, filed on 21 Mar. 2016, titled Electrocardiogram Device and Methods", all having at least one common inventor.

BACKGROUND OF THE INVENTION

Technical Field

The present invention relates to a health care device for measuring, recording and analyzing a physiological property of a user and includes a battery management system and methods of use.

Related Background Art

As sensors for physiological data and data acquisition and data handling systems have improved and the amount of physiological data available to caregivers has expanded. It is now common practice to acquire data continuously from electronic sensors attached to patients. Examples of such sensors include temperature probes, probes sensitive to movement to detect breathing and posture, sensors that detect electrical signals from the patient such as electroencephalograms (EEG) and electrocardiograms (ECG), sensors for chemistry such as blood oxygen detectors and blood glucose levels. Sensors for detecting the location of the Patient, such as GPS receivers, and radio triangulation's data is typically acquired versus time. The signal from the sensors is often a voltage or current measurement that is passed through an analog to digital converter to provide a numeric intensity measurement versus time. The analyses look for variations or patterns in the acquired data that are indicative of a disease or abnormal state. In many cases, such as that in the case of electroencephalogram and electrocardiogram data, the data represents repeating waveform patterns. The analyses use filtering and transform techniques to extract waveform morphology, fundamental frequencies and patterns in the acquired data. The data may be acquired over periods of time from seconds to months. The sensors and data acquisition may be used for patients that are not moving, such as those confined to a bed and those in an intensive care unit of a hospital or the sensors may be attached to ambulatory patients and others, where data is collected continuously as they move about in their normal life routines. Athletes using sensors during fitness training is now common. There are a wide range of uses for the devices. In some cases, the devices are used for continuous monitoring in an intensive care situation where there is a risk of harm or death and immediate alarms are required. There are other cases where there is a need for diagnoses that might not be life threatening but still require continuous data collection. And there are cases where data may be collected intermittently. A common feature for all the situations however is that the sensors collecting the data must fit comfortably to the user and not inhibit movement by the wearer.

Current sensors still are lacking. They are generally too bulky for comfortable continuous wear and require a connection to an electronic device for storage of data and perhaps even a third device for communication and transmission of the data to a remote site for data analysis. Currently the electronic devices used for local storage are bulky and hinder free movement by the wearer. There is a need for a compact one-piece data acquisition device that can be worn comfortably by both ambulatory patients and others. There is a need for a device that does not require the user to continuously wear a secondary device for data collection and transmission to a remote site for data analysis. There is a need for a range of capabilities. There is a need for sensors that include electronics with memory and computation capabilities to give immediate feedback to a patient or caregiver, and locate the patients on a map, so that they can be reached quicker by the caregivers. There is a need for low cost sensors that have limited storage and computational where data may be collected and then downloaded for viewing and analysis off line. In some cases, the diagnoses call for data collected simultaneously from multiple sites on the user's body. There is a need for sensors that can be used as part of an array of sensors on the user. There is a need for sensors that can communicate data and/or data acquisition control signals amongst a plurality of sensors in use simultaneously.

A common feature of the data analysis for such physiological information is to look for anomalies that may indicated either a disease state or a critical state where a caregiver intervention is required to aid the patient. The latter are common in intensive care unit situations. The large amount of data being acquired from a large number of patients has required the development of automated routines to evaluate the collected data. Frequently the analysis is used to provide automated response, such as in the case of insulin dosing systems responsive to automated blood glucose measurements or in the case of pace makers where an external electrical stimulus is provided upon detection of irregularity in the patient's heartbeat. The physiological data analysis is also frequently used to trigger alarms indicating immediate action is required. There is a need for sensors that can be selected and integrated into the data analysis routines.

The extended measurement times and the use on ambulatory patients have necessitated the use of batteries to power these systems. The systems frequently consist of multiple devices such as a sensor on the patient, a wireless transmission device to send the sensor data to another recording and analysis device and a networked recording, analysis and transmission device for communication with the physician or other care giver. These devices may be mobile or stationary, but for ambulatory data there is a need that at least the sensor and a communication device that may or may not be incorporated with the sensor are battery operated. The critical nature of the data and the search for rarely occurring events requires continuous high reliability in the battery system. The battery system must be able to operate the sensors and communication devices for days at a time without interruption. In the specific example of an electrocardiogram, data is acquired over a period of days is typically referred to as a "Holter scan". The data provides detailed information on the actual number of beats of each of several morphology types, number of abnormal beats, and exact length and type of arrhythmic episodes.

The current state of the art for battery power to health monitoring devices for an ambulatory patient is to have a separate battery in each of the diverse devices. The battery may be rechargeable or disposable and there may be circuitry to maintain operation for very short intervals required to change batteries. Frequently however data acquisition is interrupted if new batteries are required. If the patient is not convenient to a supply of batteries the service interruption can be extensive including loss of data, alarm and notification capabilities. With long term monitoring the loss of a significant data interval may require repeat testing. There is a need for improvements in the battery management system used with ambulatory health monitoring devices.

The discussions here will demonstrate designs and methods applied specifically to electrocardiogram data, but those skilled in the art will readily see the applicability to data acquisition any other similar timing varying physiological data.

The device being comfortable and unobtrusive for patients increases the likelihood that the patient will continuously wear the device, which contributes greatly to diagnostic yield.

There is a need for a patch that can be comfortably worn long term. Current patch designs used for ambulatory arrhythmia monitoring use wet gel electrodes with electrolytes in solution that can irritate the skin. A strong adhesive can irritate or damage skin when removed. The adhesive can break down, the patient can sweat, humid conditions and activity currently limits patch wear time to 2 to 10 days. When the patch does fall off, it generally cannot be replaced and monitoring is discontinued. It is advantageous to be able to move the patch, or replace the adhesive during the monitoring period.

DISCLOSURE OF THE INVENTION

The present invention provides a new design for an electronic patch for physiological measurements. Size is important to comfort and unobtrusive use. An internal rechargeable battery allows elimination of enclosures for a replaceable primary cell battery. In the rechargeable variation of the design, and second device containing a charging capability can fit over the patch and perhaps even be attached to the skin temporarily during recharging. The second device can charge through induction or wireless methods or be attached electrically. The second device can also contain local and wide area radios.

The communication device utilizes a cellular or WiFi radio for wide area communications with the server. It incorporates a local area radio or other communication means for bidirectional communication with the patch (this could be radio, near field communications, optical, direct connection, acoustic etc.) This results in dramatic power consumption reduction because the proximity of the two devices enables very low transmit power. The entire radio link could also be shielded from outside electromagnetic interference further improving the link budget thereby reducing or eliminating any re-transmission required due to bit errors in the link. In one embodiment the communication device is inductively charge a rechargeable battery placed in the sensor. A rechargeable battery allows for a completely sealed device, which has advantages with respect to size and ingress protection. The communication device has a means for recharging, and charging the patch. The communicator could be affixed to the body and worn over the patch to provide wide area communications from the patch while the patient is ambulatory. Otherwise, for patient comfort, the communicator can be placed once or twice a day to transmit all collected data to the server.

In some embodiments wide area communication is used so serious arrhythmic events can be detected and treatment can occur promptly. In many cases however, a patient at risk for these events will be hospitalized and not a candidate for ambulatory monitoring. Therefore, it is sometimes desirable to transmit data over the wide area network less frequently. Data can them be transmitted more power efficiently by decreasing connection/discovery/disconnection overhead incorporated into the radio protocols. The range could also be decreased by requiring a patient interaction (pressing a button) to transmit data, ensuring proximity of the two devices. The accelerometer could detect when a patient is lying down and look for a bedside communicator, ensuring range without patient interaction at the expense of perhaps more frequent discovery attempts. In another embodiment, the patch runs a local algorithm that detects only serious arrhythmias and provokes the patient to connect or the patch itself connects to the WAN automatically.

In one embodiment the patch design provides an electronic system that can be modified for different uses. In a first embodiment the patch contains a minimalist set of electronics including analog to digital converter, microprocessor and memory. In one embodiment the patch includes memory storage and the data transfer to a computing device is through physically attaching the patch electronics to the computing device. In one embodiment the transfer is through use of a memory card. In another embodiment the transfer is through removing patch electronics and attaching the electronics to the computing device. In another embodiment the patch is connected to the computing device using a wire connection such as a USB cable. In a second embodiment the patch further includes electronics for wireless transfer of data. In one embodiment the wireless electronics include an RF transceiver that is coupled with a like RF transceiver to a receiving device. In another embodiment the patch includes a multi-channel A/D and memory modules and RF transceivers that are interconnected through Direct Memory Access (DMA). The memory modules include both short term fast access memory and longer term storage. In one embodiment the RF electronics includes the ability for communication to a receiving device and for communication amongst multiple patches located on the user's body.

In one embodiment the receiving device is also a computation device and is programmed to provide analysis of the physiological data. In another embodiment the receiving computation device includes remote communication capabilities such as through the internet, through a local area network and/or through a cellular network, and can send and receive data and programming instructions to a central location remote from the user. In one embodiment the receiving computation device is a programmable cellular device such as a cell phone that includes computing capabilities. In another embodiment the receiving computation device is located remote from the user. In a preferred embodiment there is a receiving computing device local to the user and a second computing device located remote from the user that may be accessed by a caregiver for the user. In a preferred embodiment the patch acquires heart data in the form of a multi-lead electrocardiogram (ECG) and the receiving device analyzes the received data for irregularities in the user's electrocardiogram. The caregiver may be a medical professional such as a doctor, nurse, ECG technician, etc.

In another embodiment the patch includes computation capabilities that provide a first analysis that is then used in algorithms to control the data acquisition process.

In another embodiment there is a computation device local to the user and a remote computation device that is local to a caregiver and the device local to the user uses an analysis algorithm that is a "mirror" of the algorithm on the remote computation device. The remote computation device may include an array of algorithms and a decision algorithm that selects the most appropriate algorithm for the particular patient or the particular condition of that patient. The remote computation device then sends the selected algorithm to the device that is local to the patient, thereby reprogramming the local device to use the selected algorithm for analysis.

Frequently for ECG data it is important to acquire data from a patient/user continuously over a long period of time. Battery life and management of the power system is critical to successful data collection from an ambulatory user. In one embodiment the present invention solves the challenges issues with battery life in an ambulatory health care monitoring device by having a pair of interchangeable batteries within two devices local to the patient. Typical embodiments of health care devices include a portable device including sensors attached to the patient and a communication and/or computation device that may or may not be portable. There are generally size constraints on the device with the attaching sensors as the patient must wear this device even while active. A secondary communication device may not have such size constraints especially if the secondary communication device is a central communication station that only intermittently must communicate with the worn device. In one embodiment of the invention the size constrained device includes a battery that is interchangeable with a spare battery contained in the secondary device

MODES FOR CARRYING OUT THE INVENTION

Figure 1:
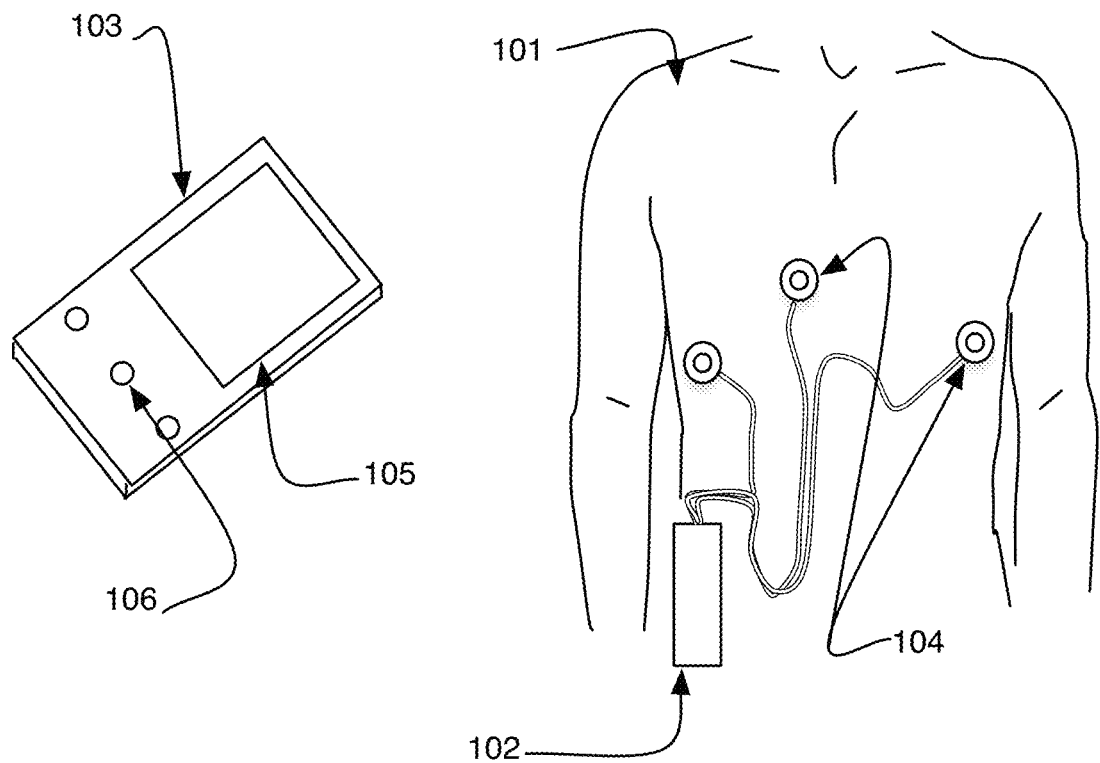
FIG. 1 shows prior art hardware.

Referring to FIG. 1 in prior art, a monitoring sensor 102 is attached to a patient 101. The Monitoring sensor includes sensors 104 attached to the patient. The sensor device 102 is in communication with a secondary device 103. The secondary device includes input and output means such as buttons 106 for inputting information and triggering events and means for viewing status 105. Non-limiting examples of sensors included in the sensor device 102 are voltage sensors for detecting electrocardiogram and electroencephalogram and respiration information, optical sensors to measure for example blood oxygen content optically, and chemical sensors to measure pH or blood glucose, potentiometric sensors to measure blood chemistry, thermal couples and thermal resistors to measure temperature and accelerometers and strain gauges to measure movement and respiration. The data from the sensors 104 is collected in a worn device 102 and transmitted to a secondary device 103. The data may be transmitted between the devices 102, 103 via wired or wireless communication. The communication may be over a local network or a global network, by blue tooth and other local and global communication means known in the art. The devices 102, 103 may further include computation capabilities that are programmed to acquire and analyze the data. The devices 102, 103 may further include communication means to communicate physiological data or the analysis results of physiological data to a central processor (not shown) where a care-giver may further view and analyze the data. The care-giver may be local to the patient or remote. The communication between the devices 102, 103 and the central processor may be through a wired communication link, a wireless communication link, a cellular communication link, a blue tooth communication link or any of the many means known in the art for data communication.

The Patch

Figure 2A:
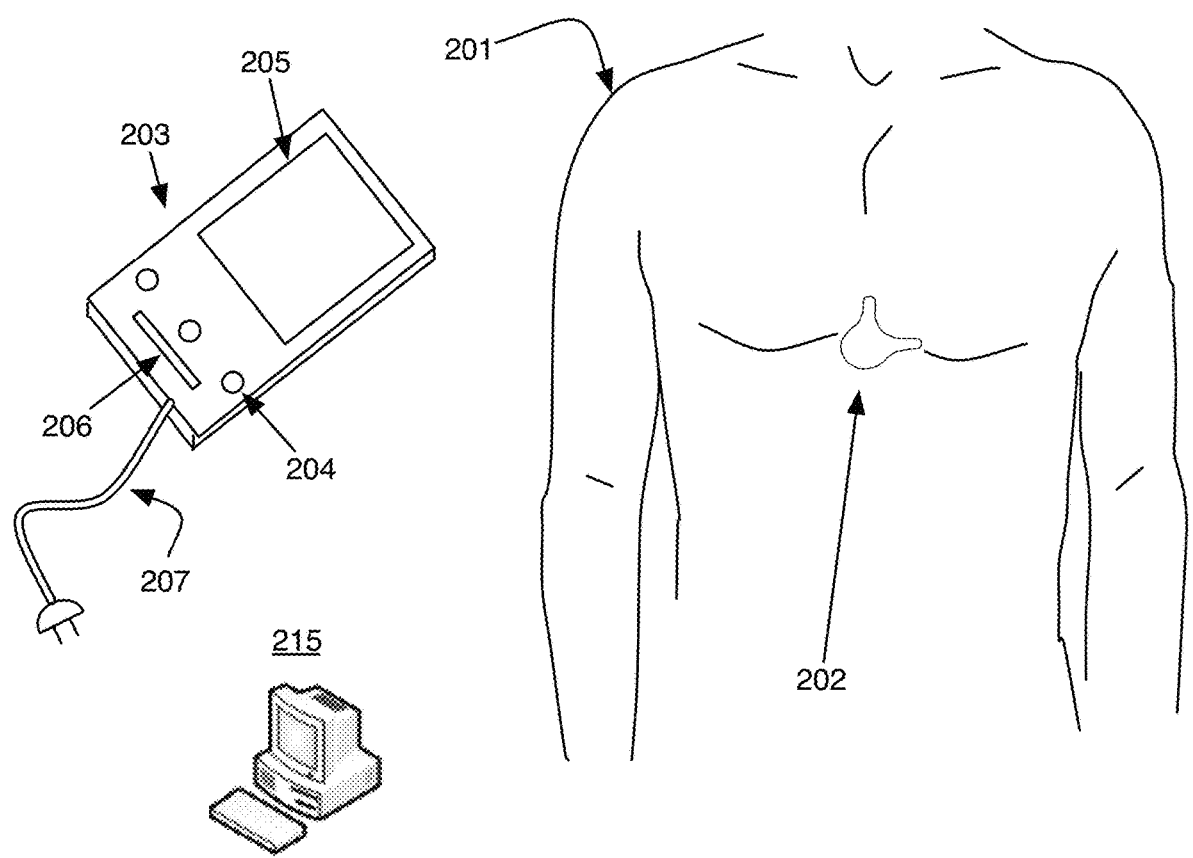
FIG. 2A shows a first embodiment for hardware of the invention.

As shown in FIG. 2A, the present invention, by contrast, includes an electrical patch 202 attached to a human subject 201. The patch 202 includes electrodes and data acquisition and storage electronics to acquire physiological data from the patient 201. As shown the patch is configured to acquire electrocardiogram data, skin temperature, and the patient's posture. Other configurations are possible, non-limiting examples of which include voltage sensors for detecting electrocardiogram and electroencephalogram information, optical sensors to measure for example blood oxygen content optically, and chemical sensors to measure pH or blood glucose, potentiometric sensors to measure blood chemistry, thermal couples and thermal resistors to measure temperature and accelerometers and strain gauges to measure movement and respiration. In one embodiment, physiological data is acquired and stored by the patch and then transferred to a communication device 203. The communication device 203 is an electronic device that transfers data received from the patch 202 to another computing device also attached to a communication device. The computing device may be local to the user 201 or may located remotely. If located remotely data may be transferred from the communication device 203 to the remote computing device by wired or wireless means.

Data is transferred from the patch to the communication device 203. The recorded data can be transferred to the communication device/receiving station by several means:

In one embodiment, the patch is physically sent in to the location of the Receiving Station, which can be equipped with an optional USB cradle 206. The patch is placed in the cradle 206, which makes contact to the electrodes of the patch 202. An electromagnet in the cradle, is sensed by a magnetic switch in the patch. The patch will then switch the function of its electrodes to act as an SPI port. Data is downloaded from the patch through the SPI Port/electrodes, to the cradle 206, which then interfaces the SPI port to the USB port of the cradle 206, and transfers the data through the USB port to the receiving station 203.

The SPI Port can also be used to activate a self-testing and diagnosis of the patch, as well as update the firmware of the patch.

In another embodiment, the patch 202 will contain an RF transceiver, which will communicate to a hand held device 203, which is normally plugged into a power outlet through a wall-plug adaptor 207, allowing its batteries to be charged while operating. Embodiments of the hand held device 203 include means to communicate to the patch such means include RF Devices, such as Bluetooth, Low Power Blue Tooth, or a custom built proprietary transceiver.

The hand held device 203 communicates to a separate receiving station/remote computing device 215 either directly through the cellular network, or by attaching to Wi-Fi network at the user's/patient's location. In another embodiment the hand held device 203 is a programmable cellular telephone. In one embodiment, the hand held device 203 is placed near the patient's bed, and data recorded during the day by the patch, is transferred through the hand held device to a remote computation device/receiving station 215, every night while the patient sleeps.

In another embodiment data is transferred by moving the hand held device 203 close to the Patient for several hours a day.

The battery condition of the patch 202 and communication device 203 is transmitted to the Receiving Station 215, allowing the monitoring center location of the receiving station 215 to inform the Patient 201 if the Patch's Battery needs to be replaced.

The communication may also be through a direct physical link such as a wired link between a port (not shown) on the patch 202 and the communication device 203. The communication may be through removal of a memory device from the patch 202 and insertion of the memory device in a slot 206 on the communication device. The communication may also be through a physical connection on the patch 202 such that the patch itself is plugged into a slot 206 on the communication device. Communication may also be through remove of a portion of the electronics on the patch 202 and physically connecting the removed electronics to the communication device. In another embodiment the patch is used without a communication device 203. In one embodiment the patch is prescribed by a caregiver and delivered to a user and then attached to the user. After a preselected span of time the patch is removed and returned to the caregiver ho downloads data from the patch either to a communication device similar to that shown in FIG. 2 or the data may be downloaded directly from the patch 202 to a computing device 215. The communication to the computing device may be the same as any of the modes described for communication to the communication device 203.

Figure 2B:
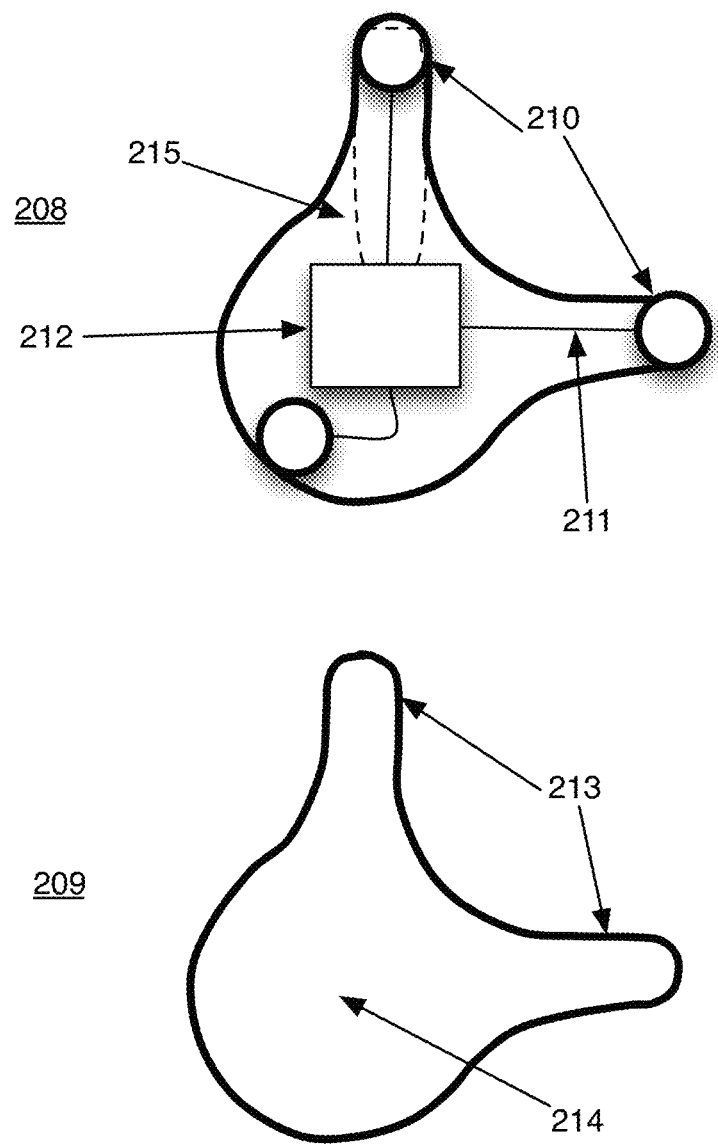
FIG. 2B shows details of a patch embodiment used in FIG. 1.

The communication device 203 includes a user interface 204. The user interface can be used to trigger the communication device to send a signal to a remote location as well as to control data acquisition local to the user 201 through the patch. The communication device may include computation electronics programmed for analysis of the electrical signal received from the patch 202. In another embodiment the computation electronics are included in the electronics of the patch itself. The communication device also includes a connection 207 to a power supply. The connection 207 is shown as an electrical plug, but other power supplies may be used instead such as a battery power supply and solar panel, both, either incorporated in the communication device 203 or attached to the communication device. More details of the patch are shown in FIG. 2B. The bottom view 208 shows an electronics module 212 and three electrodes 210. The electrodes are connected by wires 211 to the electronics module. In practice the configuration may include more or fewer electrodes although two electrodes are required to provide a voltage measurement versus some reference. Any of the three electrodes may be used as a reference electrode for voltage measurements to be made by the other two. The electronics module 212 may be permanently attached to the patch or may be removable. In one embodiment a memory device (not shown) may be inserted into the electronics module 212 for data collection and then removed for downloading to a computation device. In one embodiment the electronics module is a circuit board that further includes articulated wings 215 (shown here for only one wing in dashed lines) that extend towards each of the electrodes 210 and enable direct connection of the electrodes 210 to the circuit board through spring loaded connectors (seen in FIG. 5A below). Other configurations of the electronics module are shown in later figures. In one embodiment the electronics module may be swapped to change the functionality of the patch. In a preferred embodiment the bottom of the patch is shielded with a breathable material such that only the electrodes are exposed for attachment to the user. The electrodes may be made of a variety of materials. In one embodiment the electrodes are made of conductive materials. Ag/AgCl electrodes are common in prior art but known to cause irritation after long term use. Conductive metals are often commonly used. In some cases, the metal electrodes require a conductive gel applied to ensure continuous contact. In a preferred embodiment the electrodes are dry electrodes. In one embodiment an electrode made of material selected from: titanium, stainless steel, and platinum is used. In another embodiment metallic electrodes are used with a deposit of TiN on the surface. In other embodiments the electrodes are composed of a polymer substrate, such as polycarbonate upon which a conductive coating. In one embodiment TiN is sputter coated onto the electrode base. The base may be a metallic electrode or a polymer base and the sputtered TiN makes the base conductive for measurements. In another embodiment the electrodes are non-contact capacitive electrodes. In another embodiment the adhesive layer is "pre-soaked" with electrolyte gel around the holes for the metal electrodes.

The top of the patch is shown in the second view 209 the top 214 is a flexible material chosen to protect the electrodes and electronics of the patch and chosen such that it may be firmly, but comfortably attached to the body of the user. In the preferred embodiment the top cover includes a porous fabric cover such as one made from porous polyflourinated hydrocarbon materials such as those sold as GoreTex (Gore-Tex is a registered trademark of W.L. Gore & Associates), polymer coated cloth, or porous polyethylene, woven polyesters and polyester-polyurethane copolymers such as spandex. The patch may further include adhesive strips attached to the bottom side of the porous fabric for adhesion to the user. In another embodiment, the patch further includes wound dressing or biocompatible adhesive incorporated into the bottom side of the porous cover. Nonlimiting examples of the wound dressing adhesive include 2-octyl cyanoacrylate and other cyanoacrylates such as n-butyl-2 cyanoacrylates). Other dressing adhesive materials include films, gels, foams, hydrocolloids, alginates, hydrogels and polysaccharide pastes, granules and beads as are known in the art. The combination of the solid dry electrodes such as electrodes including a TiN deposit on their surface along with use of the wound dressing adhesives has been found to provide a patch that may be worn continuously for 30 days and longer. In another embodiment the housing includes multiple articulated arms 213 with separate circuit boards connected by flexible connectors. The articulated arms 213 allow conformance of the patch to the user's body.

Figure 3:
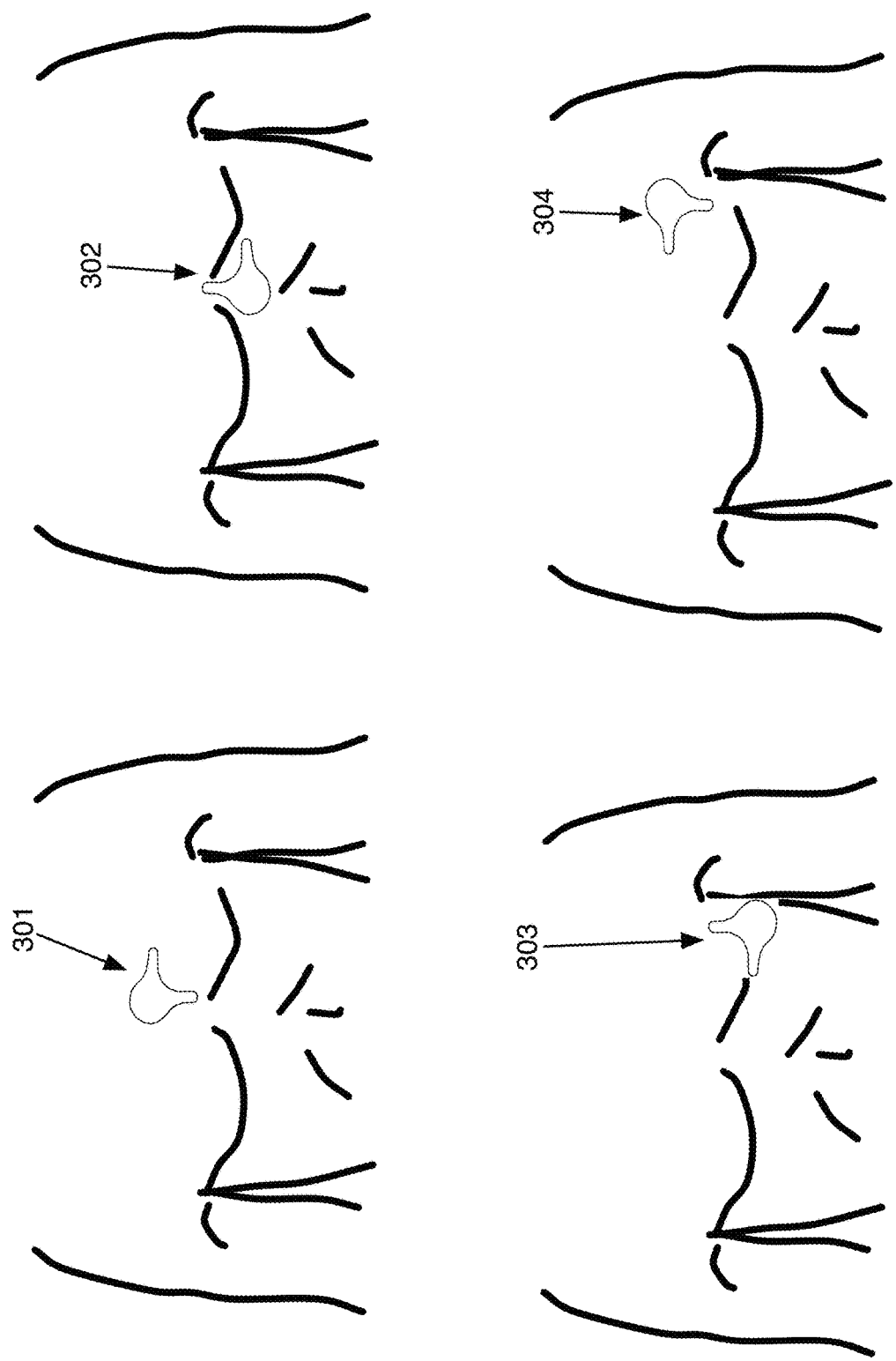
FIG. 3 shows various positions on a user for a single patch.
Figure 4:
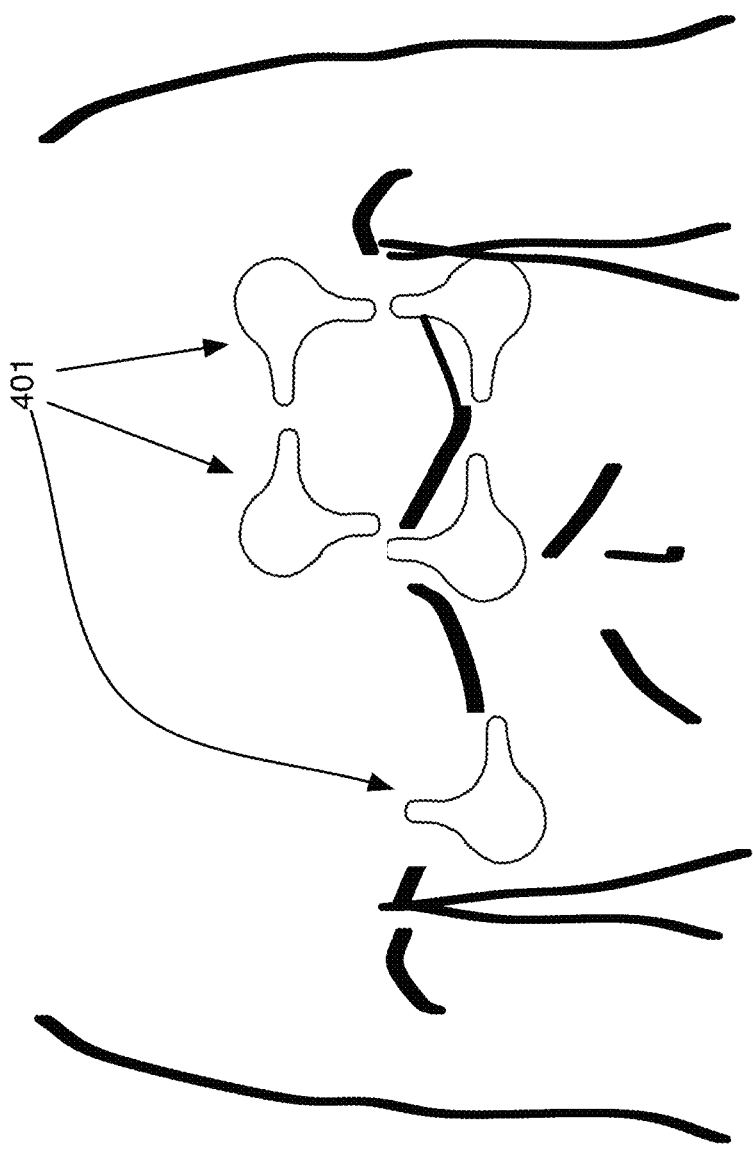
FIG. 4 shows various positions for multiple patches on a user.

The Patch may be worn in any position a preferred four positions 301-304 are shown in FIG. 3. The differing orientation allow for measurements of multiple ECG vectors. In one embodiment The ECG Vectors are sensed automatically by a version of the Patch that includes a built-in Accelerometer. In another embodiment the communication device is paired with the patch and the pairing process includes entering the position and orientation of the patch. The patch is also not limited to wearing a single patch at a time. FIG. 4 shows a user wearing a plurality of patches 401. In one embodiment the patches include an accelerometer that automatically determines the orientation of each of the patches. In another embodiment the patches include if communication not only between each patch and the communication device shown in FIG. 2, but can also communicate from one patch to the other such that an event detected on one patch can be synchronized with the detection on a second patch. In one embodiment the patches may be activated such that an event on one patch can trigger a change in the data acquisition parameters on a second patch. In another embodiment each of the patches are independently paired with the communication device and the pairing includes detecting the orientation of each of the patches and further includes entering the location of each of the patches.

Figure 5A:
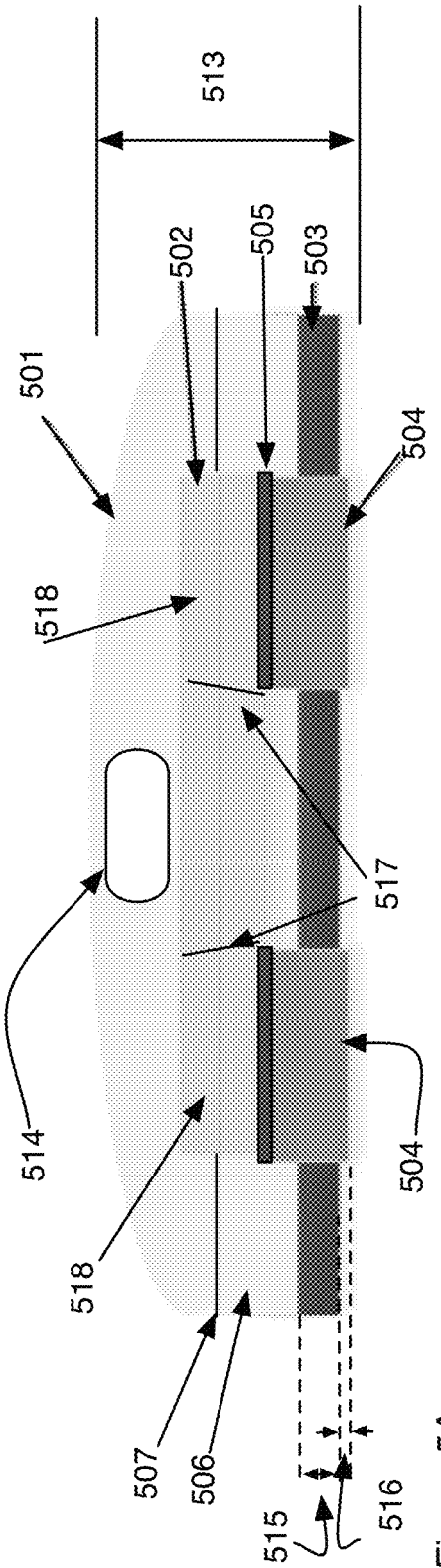
FIG. 5A is a side view cross-section showing components of an embodiment of the patch.
Figure 5B:
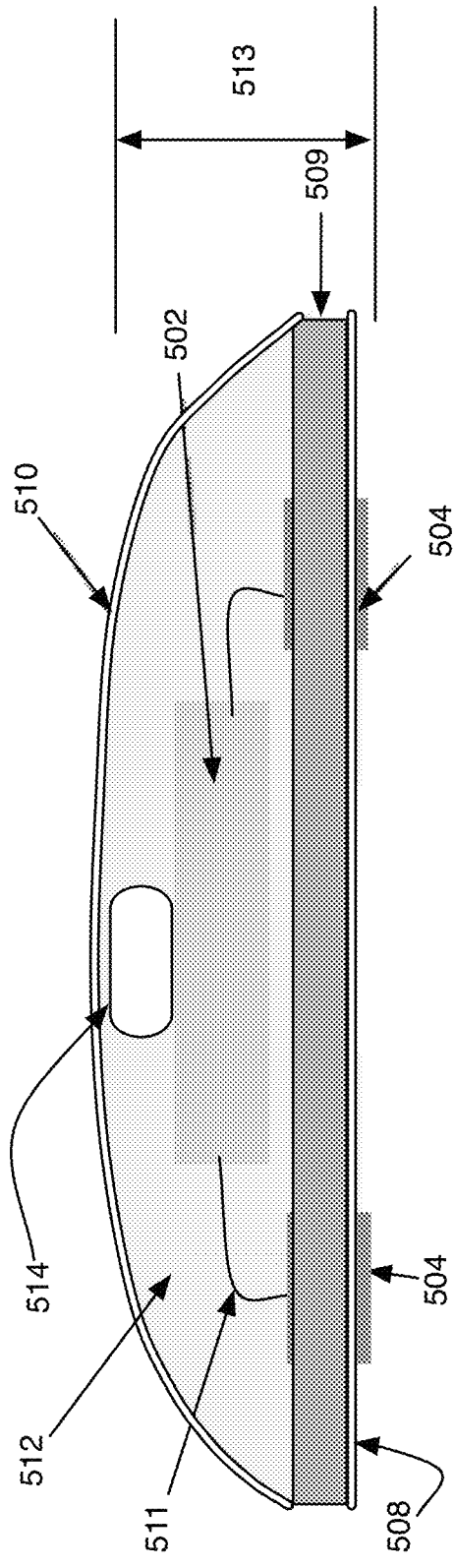
FIG. 5B is a side view cross-section showing components of another embodiment of the patch.

FIGS. 5A and 5B show two configurations of the patch in cross-sectional views. Referring to FIG. 5A, in one embodiment the patch is assembled into a clamshell plastic case comprised of a top half 501 and a bottom half 506. In the preferred embodiment the clamshell is made from an acrylonitrile butadiene styrene (ABS) polymer. The electrodes 504 along with a ground contact (not shown), will be molded into the bottom half of the case. In a preferred embodiment, the ground contact will be recessed from the outside of the case, and can only be contacted using a pogo-pin in the USB Cradle. In another embodiment an integrated rechargeable battery is used and the patch is conformally coated to the circuit board directly without an exterior top housing. Thereby making a very thin patch for comfort and unobtrusiveness. In another embodiment a portion of the patch is conformally coated and only one of the arms containing an electrode is left uncoated to include a battery housing on the side opposite the electrode.

The circuit board 502 sits on the inside of the bottom half 506 of the case, and makes contact to the electrodes 504 and the ground contact using springs 505 mounted at the bottom of the circuit board 502. In one embodiment, the circuit board is fastened to the bottom half of the case 506 using small screws, which will go through the circuit board 502, and screw into holes in each electrode 504.

The components on the circuit board 502 may include the power supply, processor, memory, accelerometer, thermistor, a giant magnetoresistance (GMR) sensor, and an RF communication chip. The battery 514 sits on top of the circuit board 502. In the preferred embodiment the battery is removable and located at center of the upper clamshell 501 to provide maximum room for a battery to include operation time between charging or replacing the battery. ECG Circuits are laid out on the top and bottom of wings of the PCB that extend towards each of the electrodes. The wings may be seen seen in FIG. 2B. The antenna (not shown) for the RF chip, will be built on a separate rigid or flex printed circuit board, which will be installed over the wings of the circuit board 502 in the top half 501 of the case.

In one embodiment the two case halves 501, 506 will be either glued together, or ultrasonically welded to each other, to provide a water-proof seal. The embodiment will further include a cavity in the housing for a battery tray to plug into the device (not shown). In one embodiment the entrance to the battery tray compartment is protected using a hydrophobic sheet of material that will enable access for changing the batteries while still protecting the interior from moisture.

In one embodiment, shown in FIG. 5A, the electronics of the patch are on a circuit board 502 and the electrodes 504 are connected to the board through connectors 505 such that the electronics may be removed from the user while the electrodes 504 remain connected and in contact with the user. The Patch is connected to the user using a layer of adhesive on a breathable flexible base material 503. In the preferred embodiment the adhesive layer on the underside of a foam 503 liner. In one embodiment the foam liner 503 includes a wound dressing adhesive. The housing for the patch is a clam shell design having a top portion 501 and a bottom portion 506 that are connected together using an interface 507. In one embodiment, the top portion 501 of the case comes in different sizes to accommodate different size batteries. This changes the thickness of the top half of the case depending on the battery needed for each configuration of the device, but leaves the bottom half 506 of the case the same for all versions of the device. In one embodiment the electronics 502 are attached to the top portion 501 of the shell such that the top portion 501 can be removed from the bottom portion 506 that remains connected to the patient/user. The top portion and the electronics can be connected to a docking station (not shown, but see 203 FIG. 2A) for data download and recharging the battery. In one embodiment a pair of top portions are used during data acquisition such that one of the pair is connected to the user for data acquisition and the other of the pair is docked for recharging and data transfer. In another embodiment the electronics remain connected to the bottom portion of the clam shell and the top portion includes the battery such that the battery can be swapped by swapping the top portion 501 of the clam shell. In this embodiment a pair of top shells are used in unison by swapping for maintaining power to the electronics through the battery management system discussed below. In one embodiment the electronics 502 further include an alert mechanism to tell the user the battery power is low and the batteries should be swapped. The alert mechanism can include an LED, vibrator or other systems known in the art to alert a user of an electronics device of some event. In another configuration of the patch, shown in FIG. 5B, the patch electronics are encased in a flexible cover 510. The electronics 502 are embedded or potted in a matrix 512 to protect from the environment. In one embodiment the electronics 502 are connected to the electrodes 504 via wire connectors. In another embodiment the electrodes are directly connected as shown in FIG. 5A. In a preferred embodiment the circuit board 502 includes flex points 517 thereby forming articulated arms 518 to which the electrodes 504 are attached. Patch designs may use combinations of the features from FIGS. 5A and 5B. As an example, the clam shell of FIG. 5A may be further covered with a flexible cover 510 as shown in FIG. 5B. In another embodiment the clam shell design of FIG. 5A may use wire connector to the electrodes as shown in FIG. 5B. Continuing with the design of FIG. 5B, the electrodes 504 are connected to a base 509. In one embodiment the base 509 is a flexible base. The base 509 is adhered to the user using a layer of adhesive 508. In the preferred embodiment the adhesive is a surgical wound adhesive as described above. In another embodiment, the electronics 502, potting 512 and cover 510 include a means to access a battery to power the patch such that the battery may be swapped. In another embodiment the patch includes a pair of batteries to maintain continuous power such that as one battery is being swapped the second battery maintains power to the electronics. Details of the battery management system are discussed below. In the preferred the patch's thickness 513 will be in the range of 8 to 12 millimeters.

In a preferred embodiment the bottom of the patch is shielded with a breathable and compressible material 503 such that only the electrodes' 504 tips are exposed for attachment to the user. The electrodes may be made of a variety of materials. In one embodiment the electrodes are made of conductive materials. Ag/AgCl electrodes are common in prior art but known to cause irritation after long term use. Conductive metals are often commonly used. In some cases, the metal electrodes require a conductive gel applied to ensure continuous contact. In a preferred embodiment the electrodes are dry electrodes. In one embodiment an electrode made of material selected from: titanium, stainless steel, and platinum is used. In another embodiment metallic electrodes are used with a deposit of TiN on the surface. In other embodiments the electrodes are composed of a polymer substrate, such as polycarbonate upon which a conductive coating. In one embodiment TiN is sputter coated onto the electrode base. The base may be a metallic electrode or a polymer base and the sputtered TiN makes the base conductive for measurements. In another embodiment the electrodes are non-contact capacitive electrodes. In another embodiment the adhesive layer is "pre-soaked" with electrolyte gel around the holes for the metal electrodes.

The width 515 of the compressible breathable material 503 is adjusted relative to the gap 516 between the bottom of the compressible material 503 and the bottom of the electrode 504 to control the pressure that is exerted pressing the bottom of the electrode against the skin of the user to maintain good contact. That is if the gap 516 is large relative to the thickness 515 more pressure is exerted in the contact of the electrode to the user when the base material 503 is adhesively attached to the user. IN one embodiment the base material is interchangeable with base materials of different thicknesses 515 and the proper thickness is selected based upon optimizing the strength of the signal measured from the electrodes 504 and the comfort of the user.

Figure 6A:
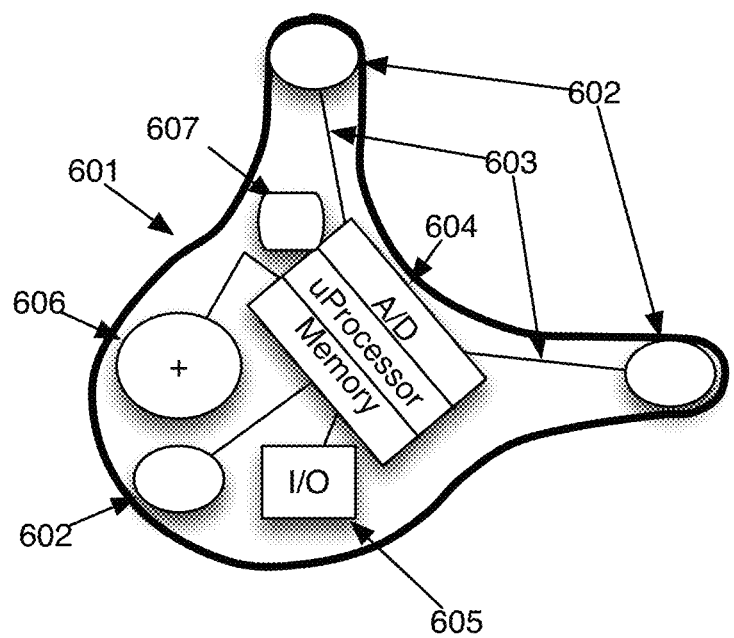
FIG. 6A is a bottom view block diagram of an embodiment of the hardware components of the patch.
Figure 6B:
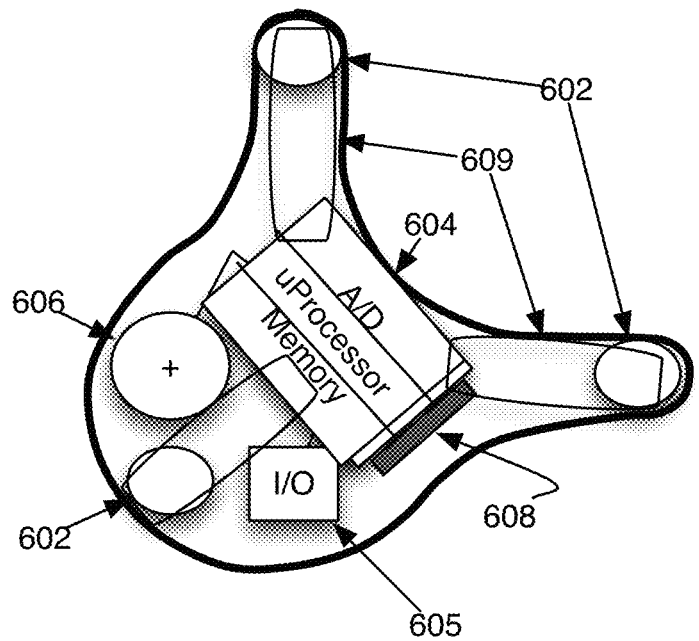
FIG. 6B is a bottom view block diagram of another embodiment of the hardware components of the patch.

FIGS. 6A and 6B show additional views and embodiments of the patch design. In FIG. 6A the patch 601 is seen to be comprised of a set of electrodes 602 that are connected to a central circuit board 604 by wires 603. The patch further includes an input/output (I/O) port 605 and a battery 606. In one embodiment the circuit board 604 includes an A/D circuit for acquiring voltage data from the electrodes 602 a microprocessor and memory to store data. The microprocessor is programmed to control the A/D to acquire and store data in memory. The microprocessor is further programmed to transmit the data to a remote processor through the I/O port. In one embodiment the I/O port is a Universal serial bus (USB) port. In another embodiment the I/O port is a radio frequency (RF) communication port. In one embodiment the RF port may be used to communicate to a local storage and data handler device as described in FIG. 2B. In another embodiment the RF port may be used to send and receive signals from a second patch similarly equipped on the same user. The microprocessor may be further programmed to analyze the data acquired by the electrodes and signal the user to whom the patch is attached a result from that analysis. In another embodiment the I/O port receives data and programming instructions from a remote device. The Patch may further include a user interface 607. In one embodiment the user interface includes a means to signal the user based on a condition detected by the microprocessor. The condition may include battery level and the signal includes an instruction to replace the battery. The condition may further be related to analysis results indicating a physiological condition as determined by programming of the microprocessor to analyze data acquired through the electrodes. The user interface 607 may further include means such as a button for the user to whom the patch is attached to send a signal to the microprocessor. The signal may initiate data acquisition. The user interface may include both a means to alert the user, such as light, buzzer or LCD or similar screen and a means for the user to input to the microprocessor. Input means can include a button or plurality of buttons. In one embodiment an accelerometer (discussed below) included in the patch is further used as the user interface such that if the user taps the patch, the accelerometer detects the motions and the microprocessor is programmed to take an action based upon that detection. In another embodiment another embodiment the microprocessor is programmed to take different actions based upon the number of taps detected in a given time period. In another embodiment the microprocessor is programmed to take a pre-selected action based upon the type of motion detected. In one embodiment if the motion detected by the accelerometer indicates the user has fallen the microprocessor may be programmed to send a signal through the I/O port to an external device to signal for help.

The patch electronics 604 can include a thermal sensing device (not shown) such as a thermocouple or thermistor for monitoring the skin temperature of the user. The temperature information is recorded periodically, and transmitted with the ECG data detected by the electrodes 602.

The patch electronics 604 can further include an accelerometer. Data from the accelerometer is recorded periodically, and transmitted to the receiving station (see FIG. 2B) along with the user's/patient's ECG. The data from the accelerometer, can indicate the position of the user (sleeping, walking, sitting, etc.) throughout the day. It can also inform the receiving station of any unusual events, such as the patient falling (Syncope), or running into objects, etc.

The accelerometer can also be used as a patient input device 607 for patient activation of events or to record markers. This can be done for instance by the patient double tapping the patch when they feel a symptom.

Each version of the patch will have enough memory to store ECG and data from other sensors, for as long as its battery 606 would last. In one embodiment lossless compression is used for storing and retrieving the ECG and data acquired by the other sensors.

The electronic configuration of the patch can be tailored to the physiological data acquisition need. In some cases, a minimal system is required for short term data acquisition and transferring the data from the patch to a computation device located either locally to the user or remotely, by a physical contact between the patch and the receiving device. Such physical contact includes plugging the patch into a USB port or moving a memory card from the patch to a computing device. In other cases, the data acquisition requirement is for long term data acquisition, such as continuous data acquisition for days or weeks at a time with both storage and analysis located directly on the patch device and wired or wireless transfer of the data on the patch to either a local computation device or a remote computation device. A range of patch configurations to handle such needs and others in between is shown in FIGS. 7-11. The features of the embodiments shown in the FIGS. 7-11 may be cumulative. That is, for example the embodiment of FIG. 8 may include all of the features described on conjunction with FIG. 7 plus additional features. Features described in other Figures of the application may also be included or combined with the features of the devices in FIGS. 7-11. As an example previous Figures described the inclusion of temperature sensors and accelerometers. These devices can also be included with the features described in FIGS. 7-11. As such, the discussion of each of FIGS. 7-11 should take into account the features described in the all other Figures in this application. And the features in all other Figures may include the features included in FIGS. 7-11.

Figure 7:
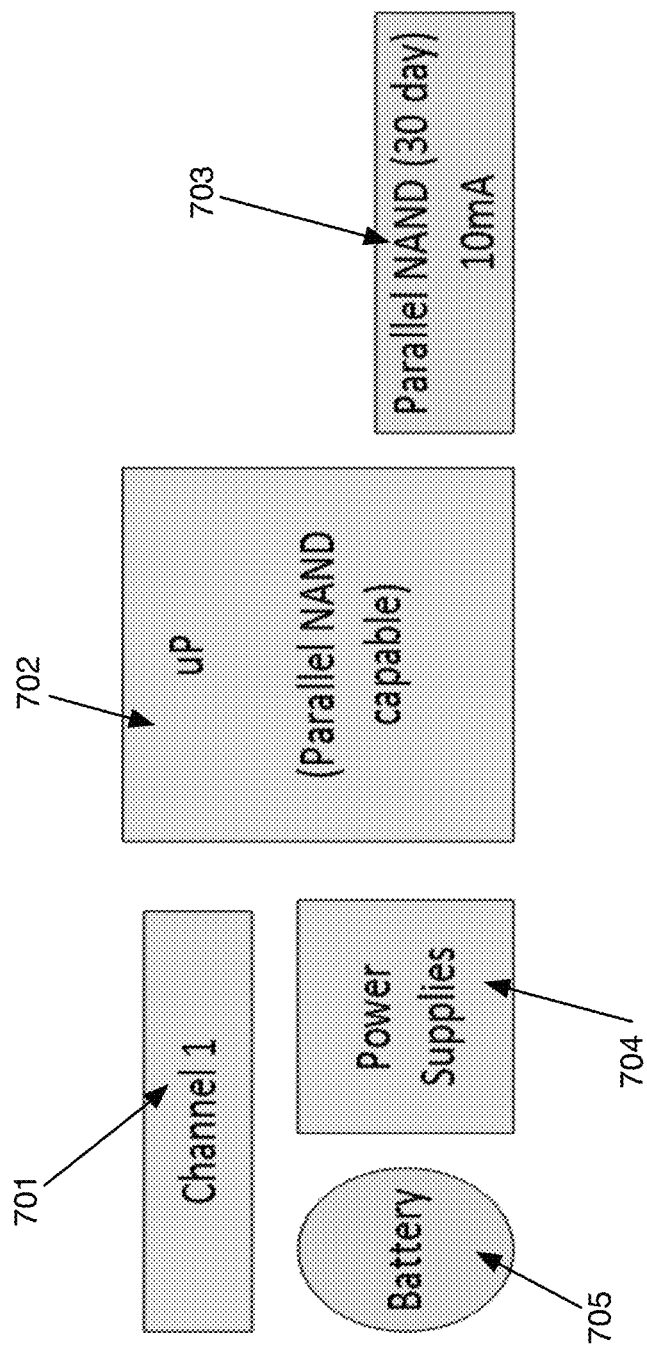
FIG. 7 is a block diagram of a minimalist version of the electronics of the patch.

Referring to FIG. 7, a first embodiment of the patch components is shown. The version is intended for a single channel data acquisition. In one embodiment the single channel is multiplexed such that the signal is from the three electrodes in the patch as described above. The single channel can also include data acquisition for temperature sensing devices an and accelerometer. The patch is comprised of an input 701 for connection to an electrode to be attached to the user's body. The input includes an A/D converter. The input is connected to a microprocessor 702 that controls the data acquisition and storage. The acquired data is stored in memory 703. In one embodiment the memory is NAND memory permanently installed in the patch. The acquired data is transferred to a communication device or processor for analysis by placing the patch in a cradle that results in an electronic connection to the patch and the data is downloaded to an intermediate communication device that transfers the data to a centrally located processor for analysis. In another embodiment the patch is connected directly to a computing device and the data is downloaded directly to the computing device with no intermediate communication device. In a preferred embodiment the connection to the patch is made through a USB port. In another embodiment, the memory 703 is a memory card that may be removed from the patch after data acquisition and inserted into an interface slot common to computing devices for download, display and analysis of the acquired data. In another embodiment the patch the electrode attached to the patch through the interface 701 can be used for download of data by connection of the electrode to a computer interface and activation of the download by the microprocessor 702. The patch further includes a battery 705 to supply power to the microprocessor and interface a required and a power supply/regulator 704. In a preferred embodiment the battery 705 is rechargeable and is recharged when the patch is attached to either a computing device or communication device for data download. In another embodiment the battery is replaceable. In one embodiment installation of the battery triggers the start of the data acquisition. The microprocessor 702 is programmed to control the data acquisition process including the input parameters such as gain and noise filters in the input channel 701, manipulate the data such that it is in a preferred format and storage of the data on the storage device 703. The microprocessor may also include programming for all data acquisition devices included in the patch with appropriate gain, filter and sampling rates. For example, the signal form an ECG electrode may be sampled at a rate of 100 to 200 samples per second whereas the microprocessor may acquire data from an accelerometer at a different rate and acquire data from a thermal sensor from at still another unique sampling rate. In one embodiment the microprocessor is further programmed to monitor the battery status and insure data is not lost even if the battery is depleted. The microprocessor may be programmed uniquely for each user.

Figure 8:
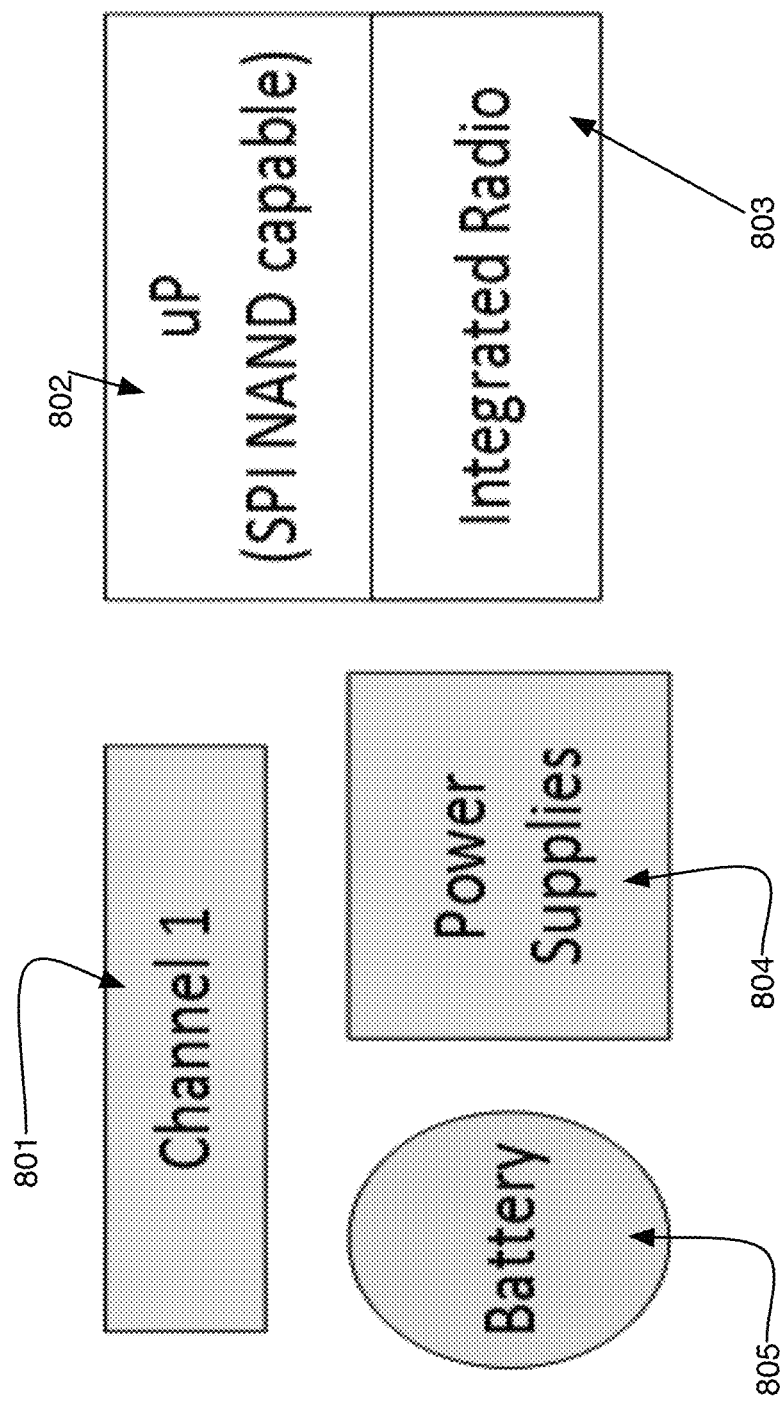
FIG. 8 is a block diagram of the electronics of the patch having a second level of capabilities.

In another embodiment shown in FIG. 8, the patch may be configured for data acquisition and streaming of acquired data to either a communication device or directly to a computing device or both. The physical appearance of the patch may be the same as for the configuration discussed in FIG. 7 and only the electronics module is swapped for the components shown in FIG. 8. The configuration is comprised of a single channel input 801, a microprocessor 802 a radio 803, and battery 805 and power supply/regulator 804. In a preferred embodiment the microprocessor is serial peripheral interface (SPI) NAND capable. The radio may be any radio frequency communication device such as blue tooth or proprietary transceiver that is paired with a similar device on a communication device or computing device. In one embodiment the pairing may be between two or more of other patches. The radio device may be used for transferring acquired data from the input channel 801 to a computing device or a communication device. The radio may also be used for communication of the status of the data acquisition, communicating status of the battery 805, communicating the status of the connection to the electrode attached to the user. The communicating the status of the electrode may include a warning that the electrode is not effectively attached to the user. Where effective attachment is based upon the strength and quality of the detected electrical signal. In one embodiment the signal to noise of the acquired signal is compared to a preselected level and if the signal to noise is less than the preselected level a signal is sent through the radio 803 to inform a user or caregiver for a user that the patch needs to be better positioned. The radio 803 may also be used for receiving control signals from an external source. The control signals maybe for starting data acquisition, stopping data acquisition, setting parameters for the data acquisition process including filter setting, acquisition frequency, and processing parameters. The radio 803 may also receive programming commands for the microprocessor. In one embodiment the microprocessor is programmed to perform analysis on the incoming data and a signal is sent by the microprocessor through the radio to inform the user or the user's caregiver of the health status of the user based upon the physiological data acquired through the incoming channel 801. In one embodiment multiple devices may be connected to the input channel 901 and multiplexed and controlled by the microprocessor to sample the devices in turn, perhaps at different sampling rates. In one embodiment the microprocessor is programmed to change the sampling rate on one of the connected devices based upon comparison of the signal received from a different device. In one embodiment the different devices are one separate patches.

Figure 9:
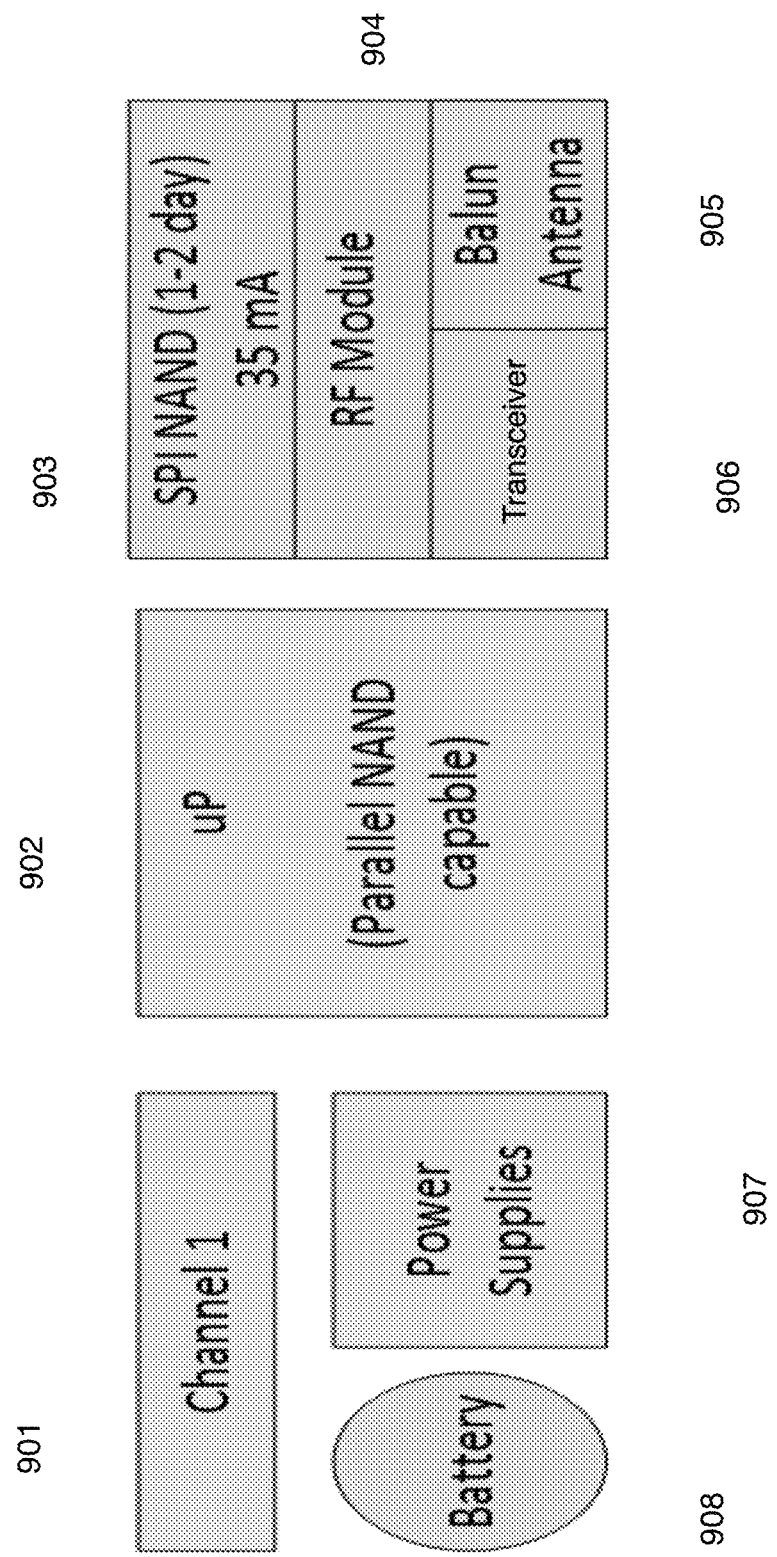
FIG. 9 is a block diagram of the electronics of a patch having approximately 2 days of data memory.

Referring now to FIG. 9 a system with additional electronic features and capabilities is shown. The configuration shown here is for a single channel device that includes limited memory. As shown in the Figure one embodiment includes memory limited to acquire data from the user for 1 or 2 days at the programmed sampling rate. As in the previous figures the device configuration includes an input channel 901 for acquiring data from measurement devices included in the patch. Measurement devices may be the three or more electrodes shown on the patches in previous Figures for ECG measurements, as well as thermocouples or thermistors, accelerometers, a magnetoresistance (GMR) sensor, and electrodes for other measurements including EEGs. The input channel 901 is connected to a microprocessor 902. In the preferred embodiment the microprocessor is Parallel NAND capable. The configuration further includes a SPI NAND memory. In one embodiment the memory 903 includes enough capacity for 1 or 2 days of data acquisition at a pre-selected sampling rate. The configuration further includes an RF communication module 904 such as a near field communication module or radio communication model such as that sold by Bluetooth corporation. The configurations further include a transceiver 906, such as those sold by Nordic Semiconductor. The configuration also includes a Balun Antenna 905. Power is supplied by a battery 908 and a power supply/regulator 907. The configuration enables transfers both to and from the patch by both wired, through connectors to the input 901 and through the RF module and the transceiver. The antenna 905 extends the range of the wireless communication such that the user/patient may wear the patch and either continuously or at preselected intervals transfer data to either an intermediate communication device or to a computing device. The SPI NAND memory module may also be used to transfer data if the device is configured as a removable memory card. In another embodiment the SPI NAND includes a connector port such that data may be transferred by a wired connection to an intermediate communication device or to a computing device.

Figure 10:
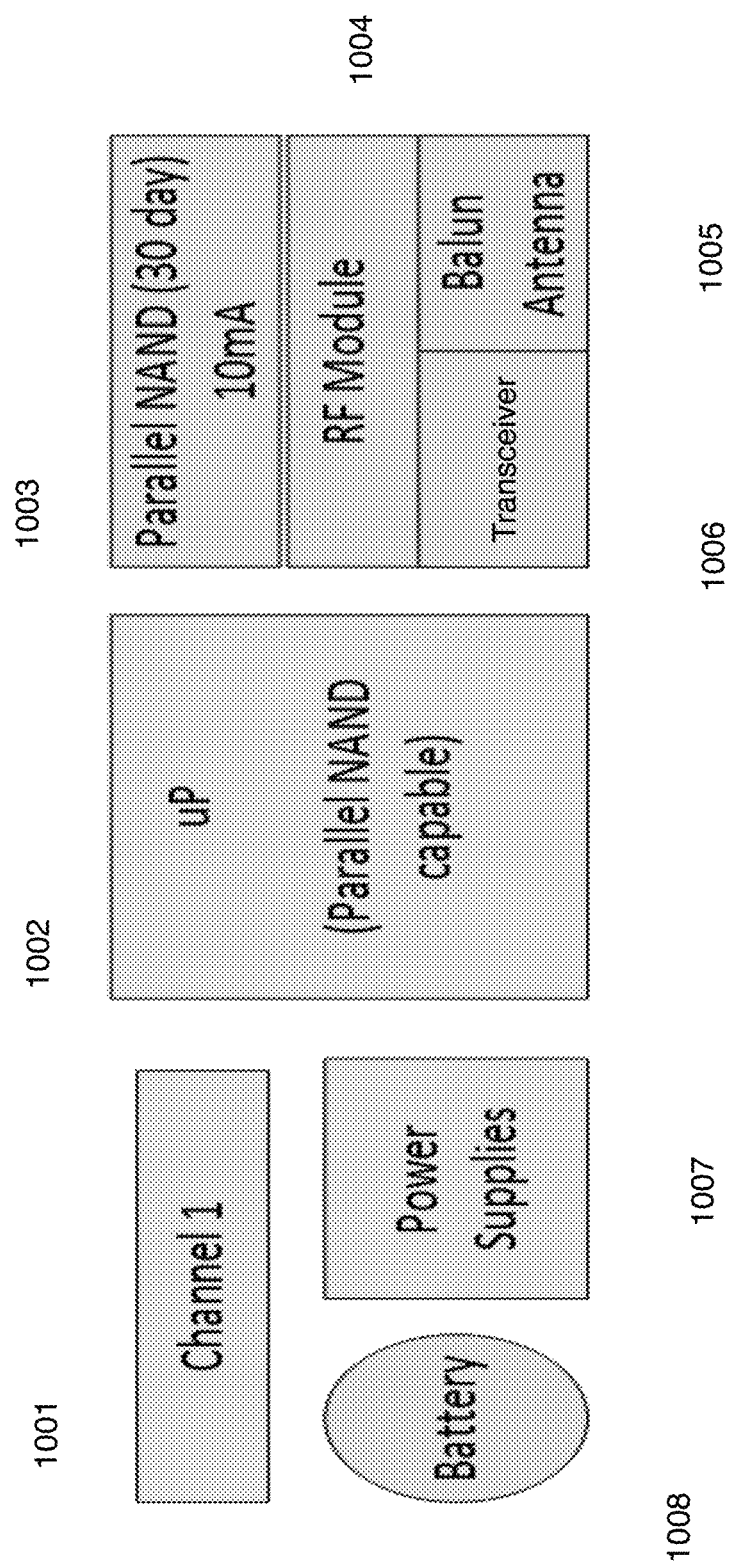
FIG. 10 is a block diagram of the electronics of a patch having approximately 30 days of data memory.

Another configuration is shown in FIG. 10. This configuration includes all the features of FIG. 9: a single channel input port 1001, a microprocessor 1002, memory 1003, the RF module 1004, the antenna 1005, the transceiver 1006, power supply/regulator 1007 and battery 1008. A difference between this configuration and that of FIG. 9 is that this configuration includes memory that would be sufficient for 30 days of data acquisition. Other features, although nominally the same, would also be modified to manage 30 days of continuous data acquisition. Non-limiting examples include more processing capabilities in the microprocessor such that during the 30-day data acquisition period the device may provide updates and alarms based upon local, on the patch, analysis of the acquired data.

The processor may be further programmed to manage the battery power supply and send signals through the RF Module or the transceiver as to when the battery 1008 needs to be changed or recharged. The RF module or the transceiver may be sued to stream the data to a remote computing device for analysis of the acquired data and they may further be used to receive data acquisition and programming instructions. In one embodiment analysis programs on the patch are "mirrored" such that the remote computing device can perform identical data analysis as is done locally. In one embodiment the remote computing device can transfer new analysis programs to the patch of FIG. 10 thereby changing the mirrored analysis programs on the fly during data acquisition.

Figure 11:
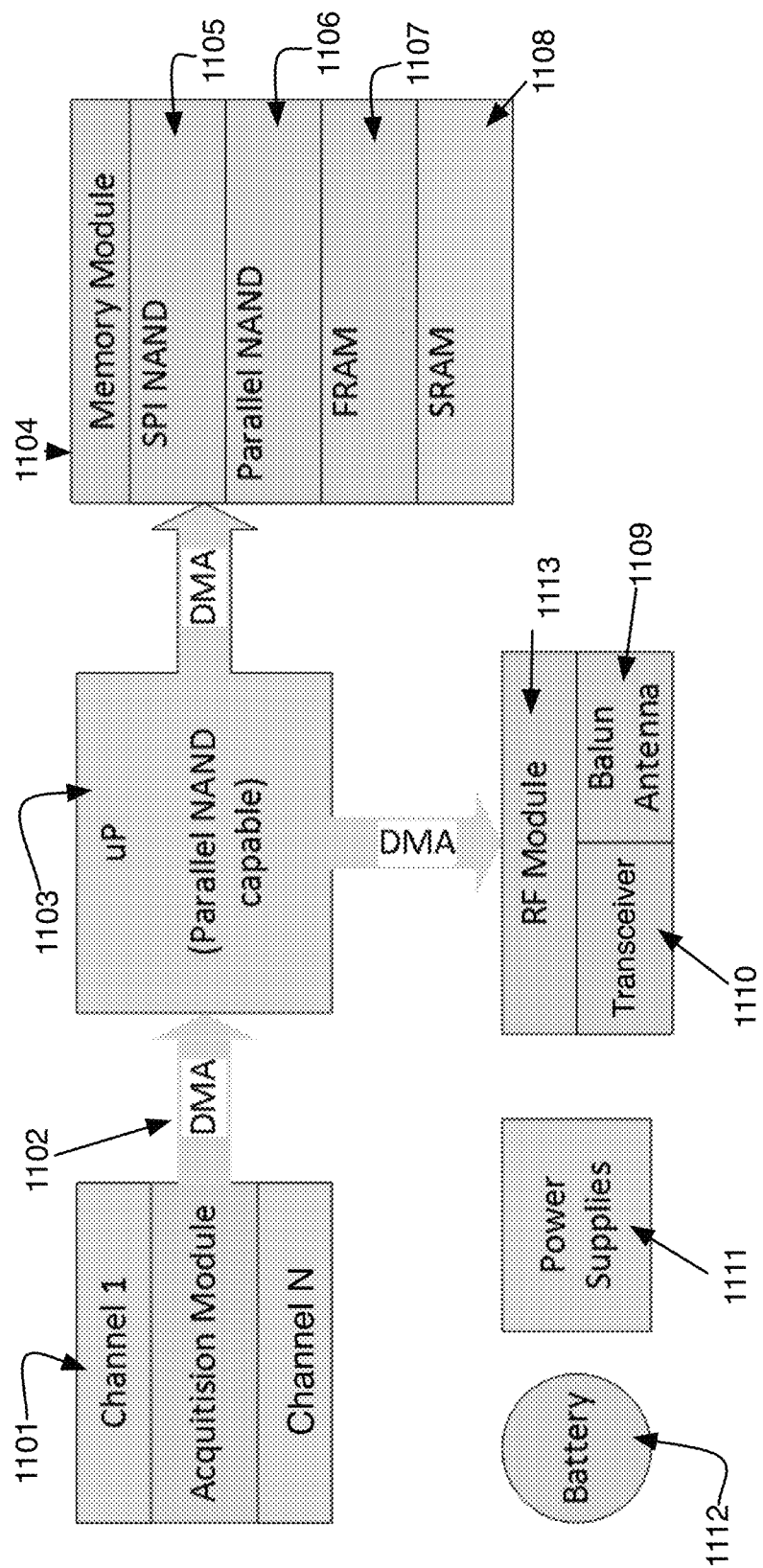
FIG. 11 is a block diagram of the electronics of a patch having multiple options for data and programming memory storage.

FIG. 11 shows a configuration with additional features to those shown in FIGS. 7-10. The input 1101 includes multiple channels 1-N. Direct memory access (DMA) 1102 is used for the connection to the microprocessor 1103. DMA enables continuous data acquisition without microprocessor intervention thereby allowing multitasking such as analysis algorithms to run on the microprocessor while data is simultaneously being acquired from the input channels 1101. Similarly, there is a DMA connection to the memory module 1104. The memory module may include one or a combination of the memory types, including SPI NAND 1105, parallel NAND 1106, ferroelectric random access memory (FRAM) 1107, and static random access memory (SRAM) 1107. The size or amount of memory is selected for the intended purpose. Patch designs can be used for both short term, less than a day, to long term, greater than 30 days, data acquisition and storage. The data may be transferred from the on board memory 1104 either by physically removing a memory device from the patch and inserting it into a computing device or intermediate communication device, or through a wired connection between the patch and the computing device or intermediate communication device or through wireless transfer. For wireless communication the patch further includes an RF module 1113. The components of the RF module may be any of those already discussed. In the example shown a transceiver 1110 with a Balun Antenna 1109 is used. The transceiver would be paired with a transceiver on a computing device or intermediate communication device for transfer of data from the patch and for communication to the patch. Communication to the patch includes programming instructions, data acquisition parameters, alerts regarding battery level, etc. In one embodiment the patch further includes an alert device, such as a light or vibrator, to instruct the user to change the battery or otherwise service the patch. The patch includes a battery 1112 connected through a power supply/regulator 1111 to provide power to the electronics.

Battery Management

Figure 12:
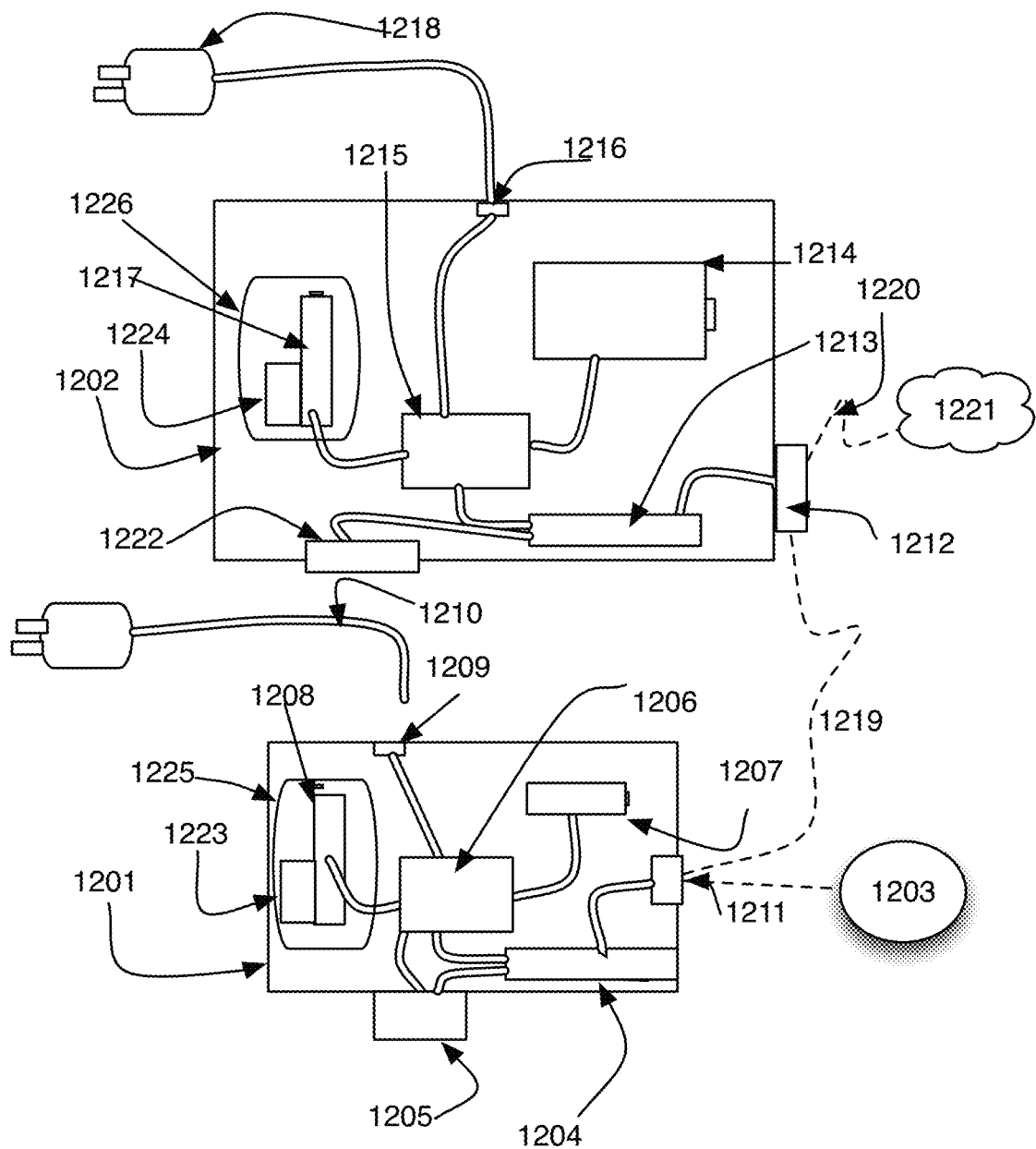
FIG. 12 is a block diagram of a physiological data acquisition device using new electronics including an invented battery management system.
Figure 13:
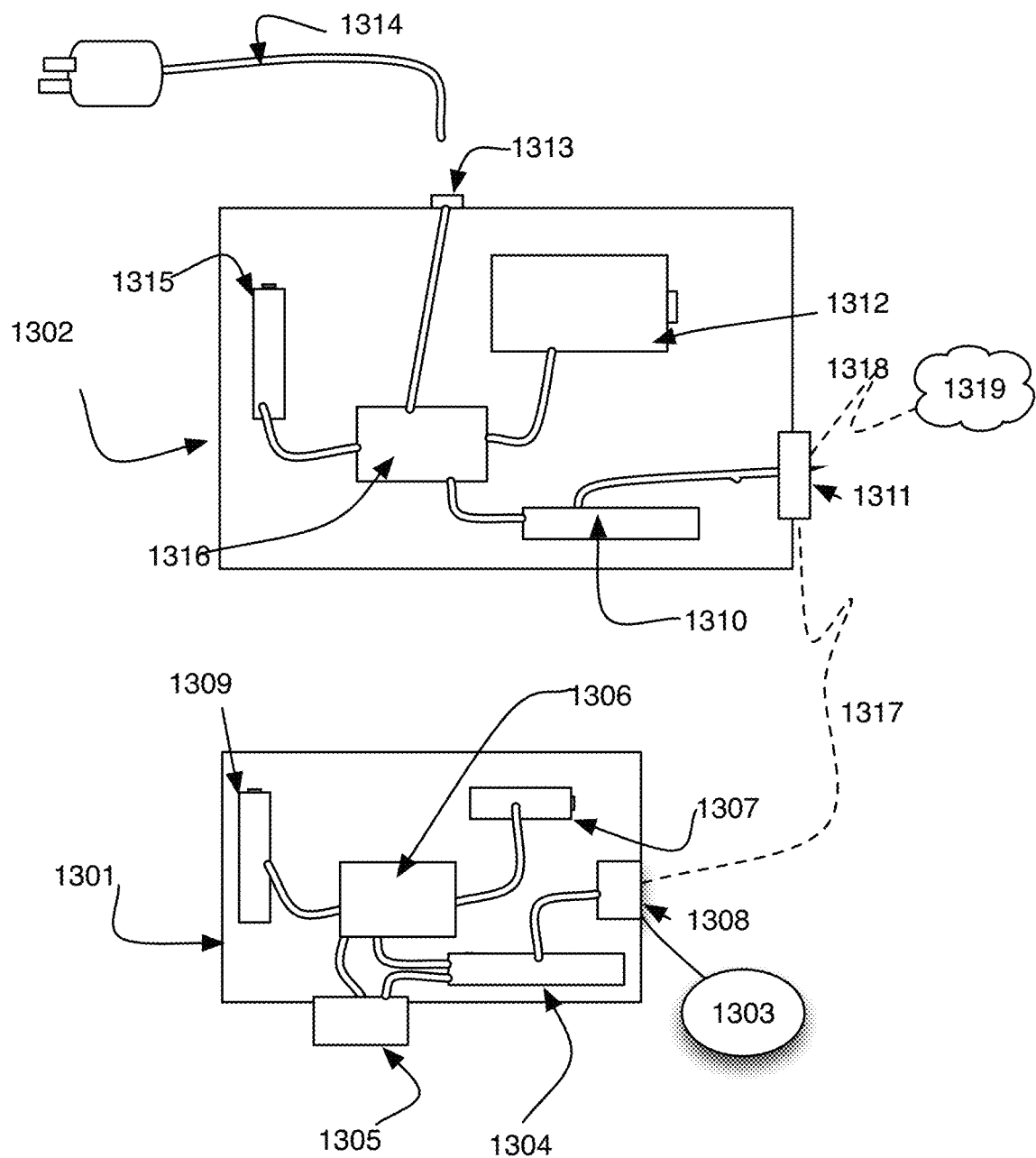
FIG. 13 is a block diagram of another embodiment of a physiological data acquisition device using new electronics including an invented battery management system.
Figure 14:
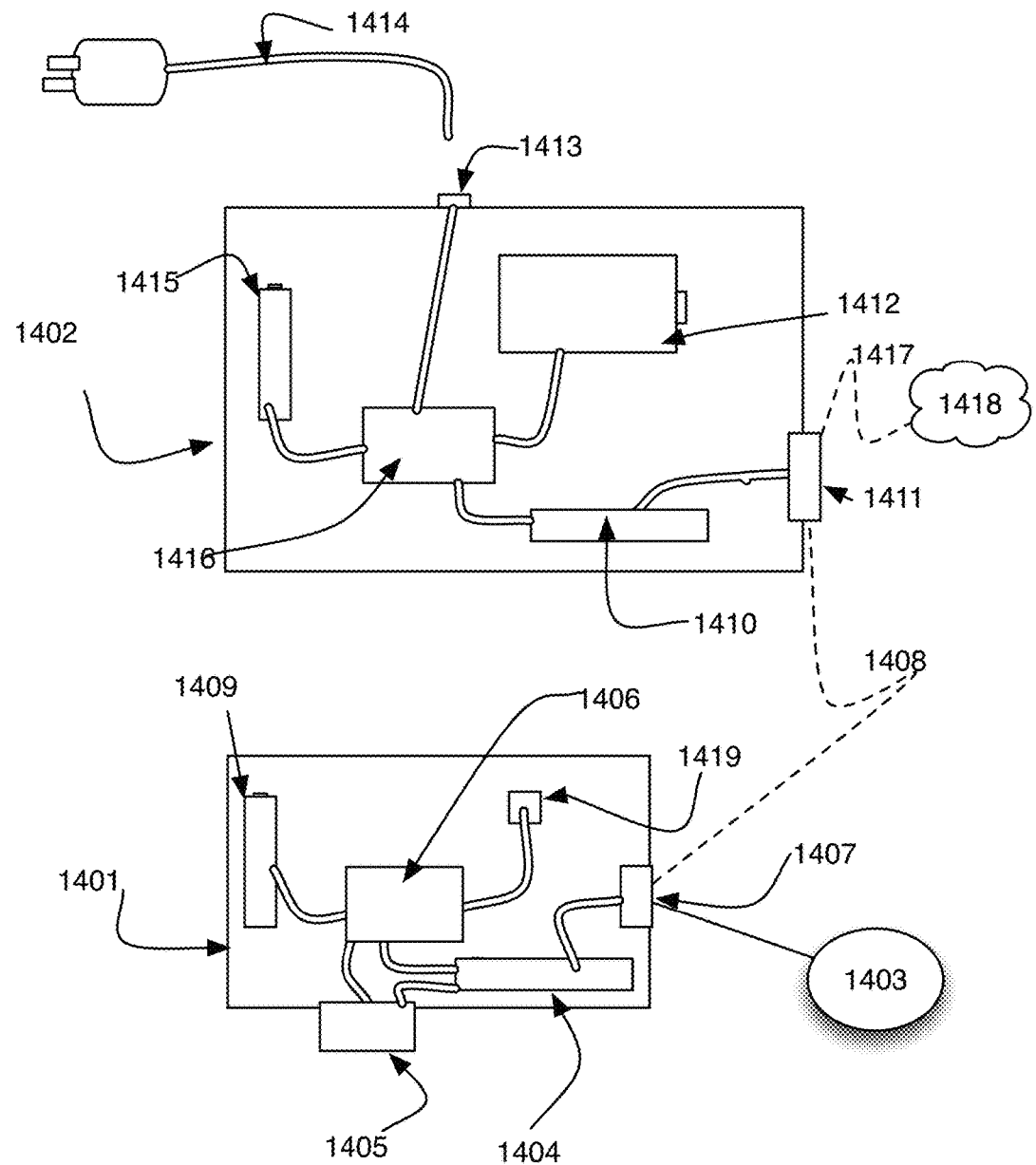
FIG. 14 is a block diagram of a physiological data acquisition device using new electronics including an invented battery management system.
Figure 15:
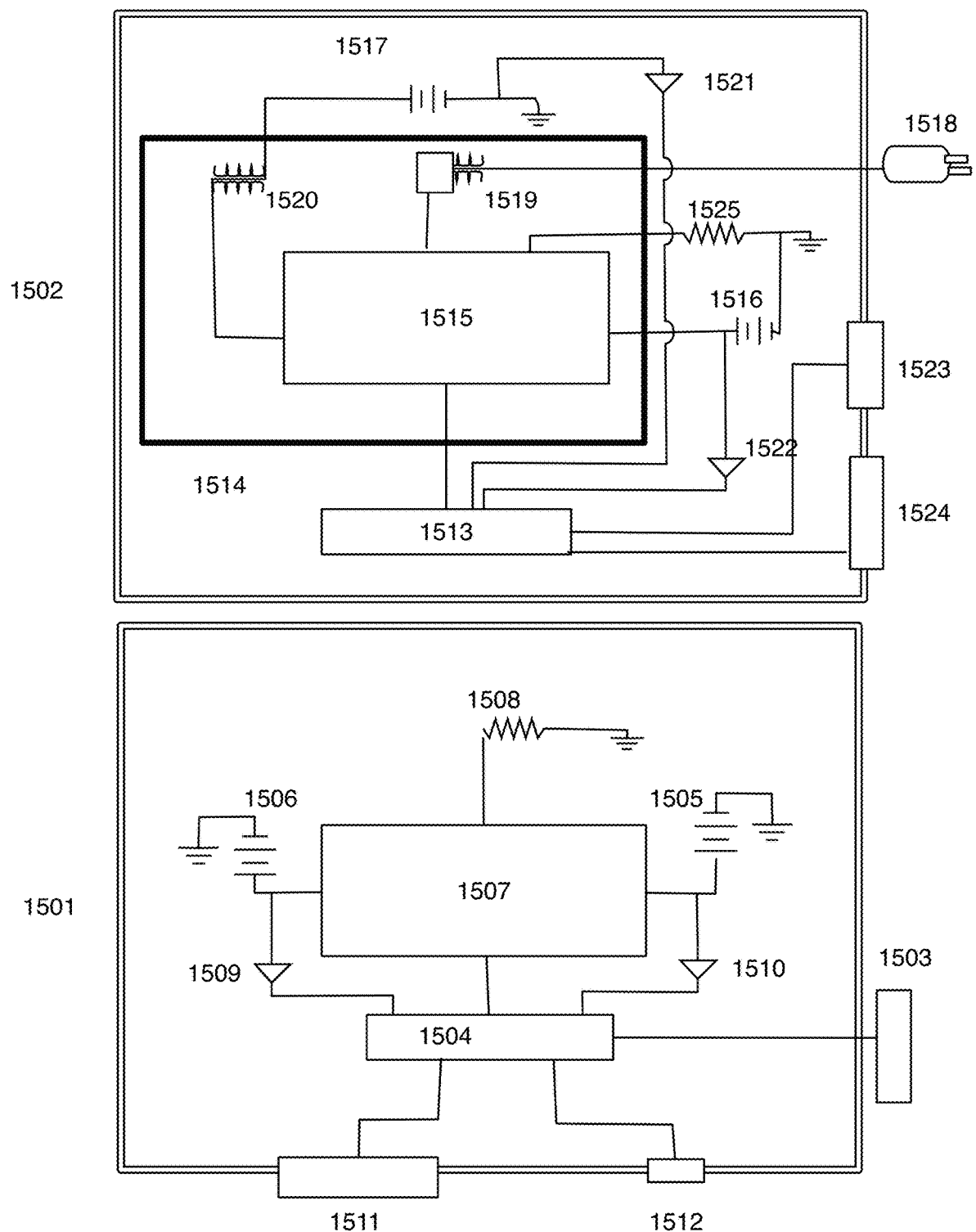
FIG. 15 is a block diagram circuit diagram for the devices of FIGS. 12-14.
Figure 16:
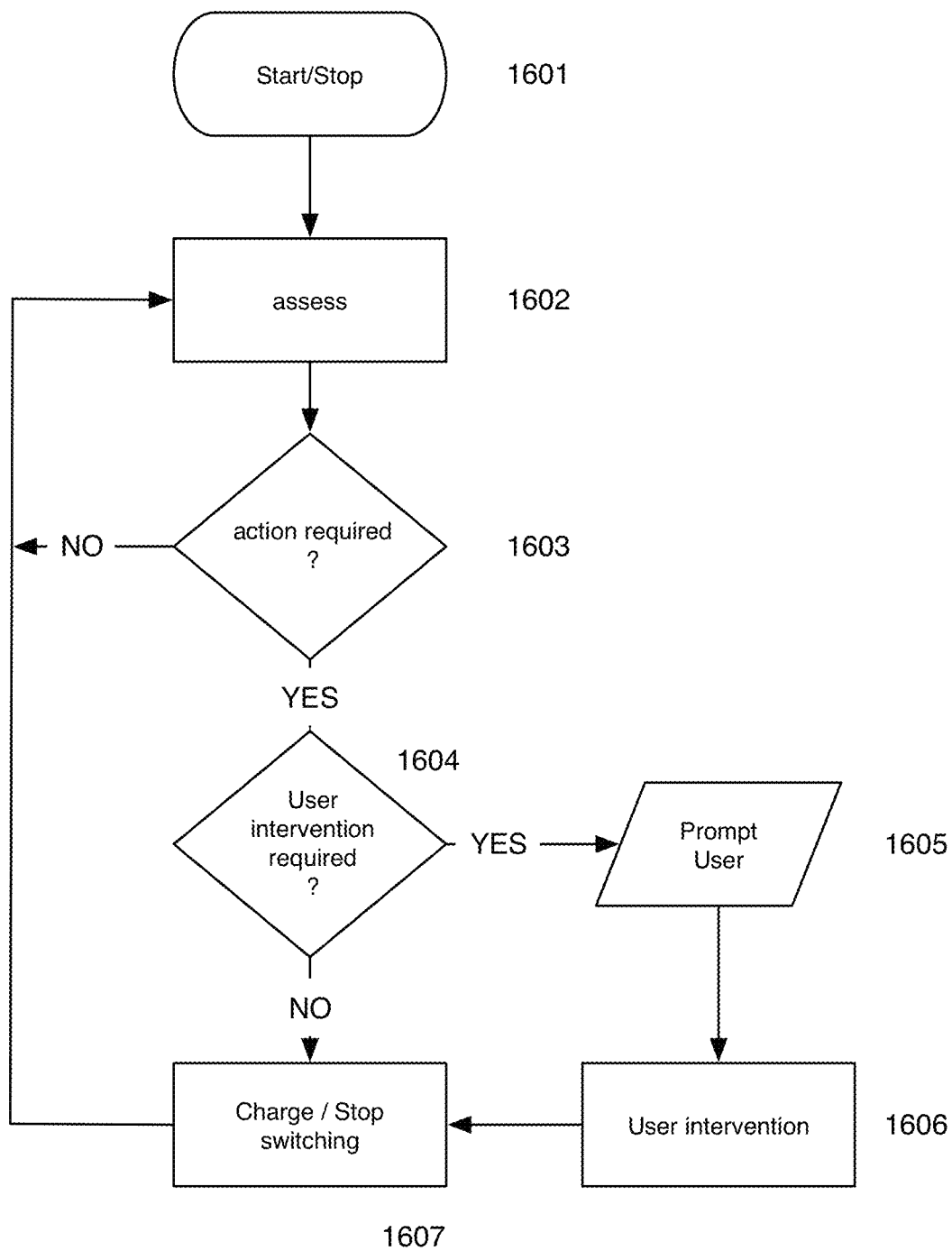
FIG. 16 is a flow chart for use of the battery management system of FIGS. 12-15.
Figure 17:
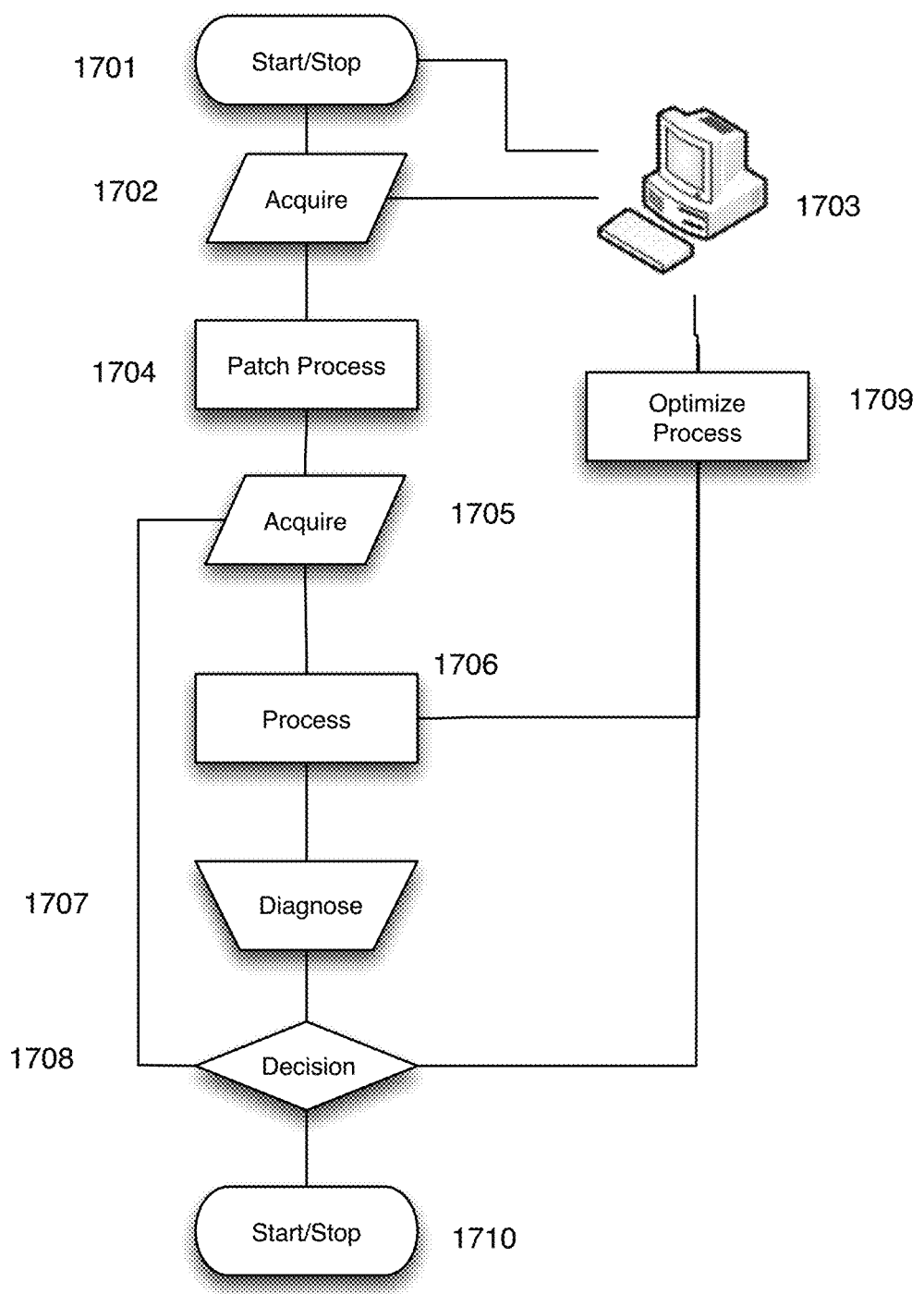
FIG. 17 is a flow chart of the algorithm management system for the patch design.

Referring now to FIG. 12 a first embodiment of the battery management aspect of the invention showing details of the devices 202 and 203 of FIG. 2. The patch 1201 is worn by the patient for physiological data acquisition and the secondary device 1202 is in the locality of the patient. In one embodiment, the patch 1201 further includes batteries 1207, 1208 to power the device. In one embodiment a first battery 1207 is used to power the device through normal operation and the second battery 1208 is used to power the device when the first battery 1207 is depleted. The device further includes a power management circuit 1206. The circuit 1206 includes input devices such as analog to digital converters that measure the state of charge of the batteries 1207, 1208 and switches that connect a battery to the other devices 1203, 1204, 1205, 1211 that require power to operate. In one embodiment the power management circuit 1206 further includes a processor that may be programmed to route power from either the first battery 1207 or the second battery 1208. The program switches between the first battery and the second battery when the state of charge of the first battery falls below a pre-selected level and the state of charge of the second battery is above a pre-selected level. In another embodiment the user is notified through the input/output device 1205 when the source of power is switched from the first battery to the second battery indicating to the user that the device is now on "reserve" power as only a single battery has sufficient power to operate the patch 1201. The device further includes a connector 1209 that may optionally be connected to an external power source 1210. Non-limiting exemplary external power sources include an electrical outlet plug, and a USB connector that can provide power and a third battery external to the patch 1201. In one embodiment the power management circuit 1206 is programmed to switch between the external power source 1210 connected through connector 1209, the first battery 1207 and the second battery 1208 based upon the state of charge of the first battery, the second battery and pre-selected parameters. In another embodiment the batteries 1207, 1208 are removable and may be swapped with a fully charged battery. In one embodiment the second device 1202 includes a battery 1217 that may be swapped with one of the batteries 1207, 1208 or both. In another embodiment the power management circuit 1206 indicates to the user through the I/O device 1205 that the user should swap a battery 1207, 1208 with the second battery 1217. In another embodiment the programmed control of the power management circuit is included in the processor 1204 rather than in a second processor included in the power management device 1206 itself.

The second device 1202 is for acquiring physiological data from the first device and evaluating or otherwise processing the physiological data and/or transmitting that data elsewhere as to a centralized facility remote from the patient and the devices 1201, 1202. The second device 1202 is comprised of communication port 1212 that is in communication 1219 with the patch 1201. The communication 1219, as already discussed, may be by wired or wireless means as are known in the art. The communication port also provides a means of communication to a remote or centralized facility 1221.

The communication path 1220 to the remote facility may be by wired or wireless means such as through a local network, a global network either of which may be connected to the Internet. The communication may also be through a local wireless network such as Bluetooth technology (Bluetooth is a registered trademark of BLUETOOTH SIG, INC.) or through a global wireless communication network such as a cellular network. The device 1202 is further comprised of a processor 1213 that is programmed to control all the functionality described herein and ascribed to the second device. The processor is connected to a power control circuit 1215 that in turn is connected through a port 1216 to an external power supply 1218, a first battery 1214 and a second battery 1217. The second battery is interchangeable with the second battery 1208 of the patch 1201. The power control circuit controls the distribution of power to the operational devices of the second unit and to supply power to a first battery 1214 when the unit is connected to an external supply 1218 and from the first battery 1214 when the unit is not connected to an external supply. The power control circuit also supplies power to the second battery 1217 which may be charged from power supplied either by an external power supply 1218 or from the first battery 1214. The device 1202 further includes an input/output means 1222 to communicate to the user and to accept input as required form the user. One communication of the i/o device 1222 is the state of charge of the first 1214 and the second 1217 batteries.

Another embodiment includes a method of using the devices of FIG. 12. The sensors 1203 are attached to the user to acquire physiological data. Exemplary sensors include those for detecting temperature, movement, electrical signals such as for an electroencephalogram or electrocardiogram, chemical sensors to measure chemical attributes of the user's physiological state such blood glucose sensors, pH sensors, blood oxygen level sensors and the like. The data acquisition is initiated and the physiological data is acquired and stored in the memory of the processor 1204 or in memory separate from the processor as discussed above but not shown here. In another embodiment the physiological data is continuously transmitted through the port 1211 to the secondary unit 1202. Data is typically acquired continuously over a long period of time perhaps extending for days, weeks or longer. The power required for the data acquisition is supplied by the batteries 1207, 1208. In one embodiment power is first supplied by the battery 1208 until it is nearly depleted. The user is then instructed through the I/O 1205 to exchange the battery 1208 with the battery 1217 contained in the secondary unit 1202. During the exchange while the battery 1208 is removed, the first unit 1201 is powered by the battery 1207. Data acquisition, processing and transmittal thereby can continue without interruption. Data acquisition can thereby also continue indefinitely with continuous exchange of batteries between the units. In another embodiment both the battery 1207 and the battery 1208 are exchangeable with the battery 1217. During use, the user is instructed via the I/O 1205 which of the two batteries to exchange with the battery 1217 of the secondary unit 1202. In another embodiment the communication 1219 between the two units includes the state of the batteries 1207, 1208 1214, 1217 and power control processor either located within the power control circuits 1215 or 1206 or included in the programs of the processors 1204 or 1213 manages charge on the four batteries so as to best provide continuous data acquisition and communication.

In one embodiment the batteries 1214, 1217 1207, 1208 are each selected to optimize ease of use. In one such exemplary selection battery 1214 is a high capacity battery and batteries 1207, 1208, 1217 are low capacity batteries. Capacity defined as the watt-hours that the battery can provide to a device when fully charged and disconnected from an external power source. The high capacity battery is located in a stationary unit 1202 and may be left at times connected to an external power supply 1218 without restriction of movement of the user. A high capacity battery has the disadvantage of being bulky and more difficult to carry around. The low capacity batteries 1207, 1208 and 1217 have the advantage of being light thus offering little restriction to the user's movements, especially during continuous operation. The disadvantage of the low capacity is overcome in the present invention by the ability to conveniently swap the battery with a charged. In one embodiment the power control circuit 1215 is controlled by a program running in the processor 1213 and the power control circuit 1206 is controlled by a program running within the processor 1204. Both power control circuits include data acquisition capabilities such as an analog to digital converter that is used to measure the voltage output of each of the four batteries 1207, 1208, 1214, 1217 such that use of the batteries is optimized to maintain continuous operation. The processors are programmed to assess the state of the batteries and to select the best source of power for operating the two devices 1201, 1202 and to alert the user to take action when required. User actions includes swapping one of batteries 1207, 1208, 1217 for one another and connecting units 1201 and 1202 to an external power supply. The program initiates action based upon the states of the batteries as shown in Table 1.

What is claimed is:

1. A system comprising an electrical patch for physiological measurements of a user, said electrical patch comprising:

a) a printed circuit board that includes a microprocessor, an input port, an analog to digital converter, a power supply, a first battery, and, computer memory, said printed circuit board attached to a base made from compressible and breathable material, the base having a thickness, b) a plurality of dry electrodes, composed of a conductive metal configured to press against the user's skin, and, the plurality of dry electrodes connected electrically to the input port, and, the plurality of dry electrodes extending through, and, a distance beyond the base, and the base is interchangeable with a plurality of interchangeable bases, each interchangeable base of the plurality of interchangeable bases comprising a unique thickness, such that a selection of a corresponding base of the plurality of interchangeable bases determines the distance the plurality of dry electrodes extend beyond the base, thereby adjusting the pressure that the plurality of dry electrodes are configured to apply against the user's skin, c) a clamshell cover having a bottom, attached to the base, and a top, attached to the bottom, and, thereby encasing the printed circuit board, and, d) wherein the microprocessor is programmed to receive an electrical signal from the electrodes and store data that includes values for the electrical signal in the computer memory, and;

e) a battery management system said battery management system comprising:
   i) a second device deriving its power from a second battery, physically separate from the electrical patch, and electronically linked to the electrical patch, said second battery of a same size and type as the first battery,
   ii) a battery charger associated with the second device wherein the battery charger is connected to an energy source that can be used to charge the second battery,
   iii) a monitor for the state of charge of the first battery and the second battery, and said monitor having a signal to signal the user to swap the first and second batteries when the state of charge of the first battery is below a pre-selected level, and when the state of charge of the second battery is above a preselected level, and,
   iv) wherein the electrical patch is configured such that the first battery and the second battery are swapped by accessing the first battery through the clamshell cover without removing the electrical patch, or any other electrical components of the patch, from the user.

2. The system of claim 1 wherein the electrodes are secured to the bottom of the clamshell cover.

3. The system of claim 1 wherein the printed circuit board is attached to the top of the clamshell cover.

4. The system of claim 2 wherein the printed circuit board is attached to the top of the clamshell cover and further including a connector between the printed circuit board and the electrodes such that the top of the clamshell may be removed from the bottom of the clamshell and the printed circuit board is thereby disconnected from the electrodes.

5. The system of claim 1 wherein the base is impregnated with wound dressing material.

6. The system of claim 1 wherein the electrodes are sputter coated with TiN.

7. The system of claim 1 wherein the electrodes are made of a polymer base that is coated with a conductive metal.

8. The system of claim 1 wherein the base is removable and interchangeable with bases having a different thickness thereby adjusting the pressure exerted by the electrodes against the user's skin.

9. The system of claim 1 further including an accelerometer, said accelerometer electrically connected to the microprocessor and controlled by the microprocessor, and said microprocessor, upon receiving a signal from the accelerometer, programmed to determine the position of the user based upon the signal from the accelerometer.

10. The system of claim 1 further including a global positioning device, said global positioning device connected to and sending a signal to the microprocessor and said microprocessor programmed to determine a physical location of the user based upon the signal from the global positioning device.

11. The system of claim 1 wherein the memory is removable, and, the stored data in the memory is transferred to a computing device that is located separate from the electrical patch by physically removing the memory from the patch and attaching the memory to the computing device.

12. The system of claim 11 further including a radio device on the printed circuit board, said radio device electrically connected to and controlled by the microprocessor, and, the stored data in the memory is transferred to the computing device that is located separate from the electrical patch by a radio connection from the electrical patch to the computing device.

13. The system of claim 12, wherein the microprocessor is programmed to include an algorithm to analyze the stored data and if the results of the algorithm's analysis is outside of preselected limits to send a signal to the computing device located separate from the electrical patch, and, the computing device also programmed to analyze the stored data received from the electrical patch using the same algorithm.

14. The system of claim 13 wherein the computing device is further programmed to select an optimum algorithm for analyzing the stored data, and, when selected, to transfer the selected optimum algorithm to the microprocessor on the patch and the patch is thereby reprogrammed to analyze the stored data using the selected optimum algorithm.

* * * * *